US005723490A

United States Patent [19]

Tung

[11] Patent Number: 5,723,490
[45] Date of Patent: Mar. 3, 1998

[54] THF-CONTAINING SULFONAMIDE INHIBITORS OF ASPARTYL PROTEASE

[75] Inventor: Roger D. Tung, Arlington, Mass.

[73] Assignee: Vertex Pharmaceuticals Incorporated, Cambridge, Mass.

[21] Appl. No.: 424,819

[22] Filed: Apr. 19, 1995

Related U.S. Application Data

[63] Continuation-in-part of Ser. No. 393,460, Feb. 23, 1995, abandoned, which is a continuation-in-part of Ser. No. 142,327, Nov. 24, 1993, Pat. No. 5,585,397, which is a continuation-in-part of Ser. No. 941,982, Sep. 8, 1992, abandoned.

[51] Int. Cl.$^6$ .......................... A61K 31/27; A61K 31/17; A61K 31/70

[52] U.S. Cl. .......................... 514/478; 514/477; 514/588; 514/50

[58] Field of Search .......................... 514/50, 478, 497, 514/588

[56] References Cited

U.S. PATENT DOCUMENTS

| | | | |
|---|---|---|---|
| 3,743,722 | 7/1973 | Mohrs et al. | 424/98 |
| 4,330,542 | 5/1982 | Descamps et al. | 424/248.5 |
| 4,629,724 | 12/1986 | Ryono et al. | 514/18 |
| 4,724,232 | 2/1988 | Rideout et al. | 514/50 |
| 5,196,438 | 3/1993 | Martin et al. | 514/311 |
| 5,354,866 | 10/1994 | Kempf et al. | 546/265 |

FOREIGN PATENT DOCUMENTS

| | | | |
|---|---|---|---|
| 0 022 118 | 1/1981 | European Pat. Off. | C07C 143/822 |
| 0 181 071 | 3/1986 | European Pat. Off. | C07K 5/06 |
| 0 264 795 | 4/1988 | European Pat. Off. | C07K 5/00 |
| 0 346 847 | 12/1989 | European Pat. Off. | C07D 207/16 |
| 0 364 804 | 4/1990 | European Pat. Off. | C07D 211/30 |
| 0 468 641 | 1/1992 | European Pat. Off. | C07K 5/02 |
| 0 486 948 | 5/1992 | European Pat. Off. | C07D 213/26 |
| 0 541 168 | 5/1993 | European Pat. Off. | C07D 217/26 |
| 3542567 | 6/1986 | Germany | C07K 5/06 |
| 59-046252 | 3/1984 | Japan | C07C 103/44 |
| 59-048449 | 3/1984 | Japan | C07C 103/375 |
| 61-071830 | 4/1986 | Japan | B01F 17/46 |
| 2167759 | 6/1986 | United Kingdom | C07K 5/06 |
| 2200115 | 7/1988 | United Kingdom | C07C 103/00 |
| WO 90/07329 | 7/1990 | WIPO | A61K 31/19 |
| WO 91/00725 | 1/1991 | WIPO | |
| WO 91/18866 | 12/1991 | WIPO | C07C 237/22 |
| WO 92/08688 | 5/1992 | WIPO | C07D 215/48 |
| WO 92/08698 | 5/1992 | WIPO | C07D 215/48 |
| WO 92/08699 | 5/1992 | WIPO | C07D 215/48 |
| WO 92/08700 | 5/1992 | WIPO | C07D 215/48 |
| WO 92/08701 | 5/1992 | WIPO | C07D 215/48 |
| WO 92/17176 | 10/1992 | WIPO | A61K 31/44 |
| WO 93/23368 | 11/1993 | WIPO | C07C 275/24 |
| WO 93/23379 | 11/1993 | WIPO | C07D 217/26 |
| WO 93/23388 | 11/1993 | WIPO | C07D 303/36 |
| WO 94/04491 | 3/1994 | WIPO | C07K 13/00 |
| WO 94/04492 | 3/1994 | WIPO | C07C 311/29 |
| WO 94/04493 | 3/1994 | WIPO | C07C 317/44 |
| WO 94/10134 | 5/1994 | WIPO | C07C 307/06 |
| WO 94/10136 | 5/1994 | WIPO | C07C 317/44 |
| WO 94/18192 | 8/1994 | WIPO | C07D 401/14 |
| WO 94/19322 | 9/1994 | WIPO | C07D 209/34 |

OTHER PUBLICATIONS

R.D. Bindal et al., "Ab Initio Calculations on N–Methylmethanesulfonamide and Methyl Methanesulfonate for the Development of Force Field Torsional Parameters and Their Use in the Conformational Analysis of Some Novel Estrogens", *J. Am. Chem. Soc.*, 112, pp. 7861–7868 (1990).

R. Bone et al., "X–ray Crystal Structure of the HIV Protease Complex with L–700,417, an Inhibitor with Pseudo $C_2$ Symmetry", *J. Am. Chem. Soc.*, 113, pp. 9382–9384 (1991).

R.F. Borch et al., "The Cyanohydridoborate Anion as a Selective Reducing Agent", *J. Am. Chem. Soc.*, 93, pp. 2897–2904 (1971).

J.C. Craig et al., "Antiviral Synergy Between Inhibitors of HIV Proteinase and Reverse Transcriptase", *Antiviral Chem. and Chemotherapy*, 4(3), pp. 161–166 (1990).

S. Crawford et al., "A Deletion Mutation of the 5' Part of the pol Gene of Moloney Murine Leukemia Virus Blocks Proteolytic Processing of the gag and pol Polyproteins", *J. Virol.*, 53, pp. 899–907 (1985).

M. Cushman et al., "Delvelopment of Methodology for the Synthesis of Stereochemically Pure Pheψ[CH$_2$N]Pro Linkages in HIV Protease Inhibitors", *J. Org. Chem.*, 56, pp. 4161–4167 (1991).

D.S. Dhanoa et al., "The Synthesis of Potent Macrocyclic Renin Inhibitors", *Tetrahedron Lett.*, 33, pp. 1725–1728 (1992).

G.B. Dreyer et al., "Hydroxyethylene Isosters Inhibitors of Human Immunodeficiency Virus–1 Protease: Structure–Activity Analysis Using Enzyme Kinetics, X–ray Crystallography, and Infected T–Cell Assays", *Biochemistry*, 31, pp. 6646–6659 (1992).

B.E. Evans et al., "A Stereocontrolled Synthesis of Hydroxyethylene Dipeptide Isosteres Using Novel, Chiral Aminoalkyl Epoxides and γ–(Aminoalkyl) γ–Lactones", *J. Org. Chem.*, 50, pp. 4615–4625 (1985).

G.A. Flynn et al., "An Acyl–Iminium Ion Cyclization Route to a Novel Conformationally Restricted Dipeptide Mimic: Applications to Angiotensin–Converting Enzyme Inhibition", *J. Am. Chem. Soc.*, 109, pp. 7914–7915 (1989).

(List continued on next page.)

*Primary Examiner*—Russell Travers
*Attorney, Agent, or Firm*—Fish & Neave; James F. Haley, Jr.; Andrew S. Marks

[57] ABSTRACT

The present invention relates to a class of THF-containing sulfonamides which are aspartyl protease inhibitors. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting the activity of HIV aspartyl protease using the compounds of this invention.

18 Claims, No Drawings

OTHER PUBLICATIONS

G. Fontenot et al., "PCR Amplification of HIV–1 Proteinase Sequences Directly from Lab Isolates Allows Determination of Five Conserved Domains", *Virology*, 190, pp. 1–10 (1992).

P.G. Gassman and T.L. Guggenheim, "Opening of Epoxides with Trimethylsilyl Cyanide to Produce β–Amino Alcohols", *J. Am. Chem. Soc.*, 104, pp. 5849–5850 (1982).

E.E. Gilbert, "Recent Developments in Preparative Sulfonation and Sulfation", *Synthesis*, 1969, pp. 3–10 (1969).

A. Goldblum, "Modulation of the Affinity of Aspartic Proteases by the Mutated Residues in Active Site Models", *FEBS*, 261, pp. 241–244 (1990).

D. Grobelny et al., "Selective Phosphinate Transition–State Analogue Inhibitors of the Protease of Human Immunodeficiency Virus", *Biochem. Biophys. Res. Commun.*, 169, pp. 1111–1116 (1990).

G.D. Hartman et al., "4–Substituted Thiophene– and Furan–2–sulfonamides as Topical Carbonic Anhydrase Inhibitors", *J. Med. Chem.*, 35, pp. 3822–3831 (1992).

J.R. Huff, "HIV Protease: A Novel Chemotherapeutic Target for AIDS", *Journal of Medicinal Chemistry*, 34(8), pp. 2305–2314 (1991).

K.Y. Hui et al., "A Rational Approach in the Search for Potent Inhibitors Against HIV Proteinase", *FASEB*, 5, pp. 2606–2610 (1991).

N.E. Kohl et al., "Active HIV Protease Is Required for Viral Infectivity", *Proc. Natl. Acad. Sci. USA*, 85, pp. 4686–4690 (1988).

X. Lin et al., "Enzymatic Activities of Two–Chain Pepsinogen, Two–Chain Pepsin, and the Amino–Terminal Lobe of Pepsinogen", *J. Biol. Chem.*, 267(24), pp. 17257–17263 (1992).

K.P. Manfredi et al., "Examination of HIV–1 Protease Secondary Structure Specificity Using Conformationally Constrained Inhibitors", *J. Med. Chem.*, 34, pp. 3395–3399 (1991).

F.R. Marshall, "Computer–Aided Drug Design", *Ann. Ref. Pharmacol. Toxicol.*, 27, pp. 193–213 (1987).

J.A. Martin, "Recent Advances in the Design of HIV Proteinase Inhibitors", *Antiviral Research*, 17, pp. 265–278 (1992).

T.D. Meek et al., "Inhibition of HIV–1 Protease in Infected T–Lymphocytes by Synthetic Peptide Analogues", *Nature*, 343, pp. 90–92 (1990).

M. Miller et al., "Structure of Complex of Synthetic HIV–1 Protease with a Substrate–Based Inhibitor at 2.3 Å Resolution", *Science*, 246, pp. 1149–1152 (1989).

M. Miller et al., "Crystal Structure of a Retroviral Protease Proves Relationship to Aspartic Protease Family", *Nature*, 337, pp. 576–579 (1989).

H. Mitsuya and S. Broder, "Inhibition of the in vitro Infectivity and Cytopathic Effect of Human T–Lymphotropic Virus Type III/Lymphoadenopathy–Associated Virus (HTLV–III/LAV) by 2',3'–Dideoxynucleosides", *Proc. Natl. Acad. Sci. USA*, 83, pp. 1911–1915 (1986).

K.H.M. Murthy et al., "Crystal Structures at 2.2–Å Resolution of Hydroxyethylene–Based Inhibitors Bound to Human Immunodeficiency Virus Type 1 Protease Show That the Inhibitors Are Present in Two Distinct Orientations", *J. Biol. Chem.*, 267, pp.22770–22778 (1992).

J.B. Nichols et al., "A Molecular Mechanics Valence Force Field for Sulfonamides Derived by ab initio Methods", *J. Phys. Chem.*, 95, pp. 9803–9811 (1991).

L.E. Overman and L.A. Flippin, "Facile Aminolysis of Epoxides with Diethylaluminum Amides", *Tetrahedron Letters*, 195, pp. 195–198 (1981).

J. Palca, "Shooting at a New HIV Target", *Science*, 247, p. 410 (1990).

L.H. Pearl et al., "A Structural Model for the Retroviral Proteases", *Nature*, 329, pp. 329–351 (1987).

M. Popvic et al., "Detection, Isolation, and Continuous Production of Cytopathic Retroviruses (HTLV–III) from Patients with AIDS and Pre–AIDS", *Science*, 224, pp. 497–500 (1984).

G.H. Posner and D.Z. Rogers, "Organic Reactions at Alumina Surfaces. Mild and Selective Opening of Epoxides by Alcohols, Thiols, Benzeneselenol, Amines, and Acetic Acid", *J. Am. Chem. Soc.*, 99, 8208–18 (1977).

M.D. Power et al., "Nucleotide Sequence of SRV–1, a Type D Simian Acquired Immune Deficiency Syndrome Retrovirus" *Science*, 231, pp. 1567–1573 (1986).

N.A. Roberts, "Rational Design of Peptide–Based HIV Proteinase Inhibitors", *Science*, 248, pp. 358–361 (1990).

S. Scharpe et al., "Proteases and Their Inhibitors: Today and Tomorrow", *Biochimie*, 73, pp. 121–126 (1991).

S.K. Sharma et al., "Could Angiotensin I Be Produced from a Renin Substrate by the HIV–1 Protease?", *Anal. Biochem.*, 198, pp. 363–367 (1991).

H. Toh et al., "Close Structural Resemblance Between Putative Polymerase of a Drosophila Transposable Genetic Element 17.6 and pol Gene Product of Moloney Murine Leukemia Virus", *EMBO J.*, 4, pp. 1267–1272 (1985).

Tung et al 1995 122 CA:81141j.

THF-CONTAINING SULFONAMIDE INHIBITORS OF ASPARTYL PROTEASE

CROSS-REFERENCE TO RELATED APPLICATIONS

This application is a continuation-in-part of U.S. patent application Ser. No. 08/393,460, now abandoned, filed Feb. 23, 1995; which is a continuation-in-part of U.S. patent application Ser. No. 08/142,327, now U.S. Pat. No. 5,585, 397, filed Nov. 24, 1993; which is a continuation-in-part of U.S. patent application Ser. No. 07/941,982; filed Sep. 8, 1992, now abandoned.

TECHNICAL FIELD OF THE INVENTION

The present invention relates to a class of THF-containing sulfonamides which are aspartyl protease inhibitors. This invention also relates to pharmaceutical compositions comprising these compounds. The compounds and pharmaceutical compositions of this invention are particularly well suited for inhibiting HIV-1 and HIV-2 protease activity and consequently, may be advantageously used as anti-viral agents against the HIV-1 and HIV-2 viruses. This invention also relates to methods for inhibiting the activity of HIV aspartyl protease using the compounds of this invention.

BACKGROUND OF THE INVENTION

The human immunodeficiency virus ("HIV") is the causative agent for acquired immunodeficiency syndrome ("AIDS")—a disease characterized by the destruction of the immune system, particularly of $CD_4^+$ T-cells, with attendant susceptibility to opportunistic infections—and its precursor AIDS-related complex ("ARC")—a syndrome characterized by symptoms such as persistent generalized lymphadenopathy, fever and weight loss.

As in the case of several other retroviruses, HIV encodes the production of a protease which carries out post-translational cleavage of precursor polypeptides in a process necessary for the formation of infectious virions (S. Crawford et al., "A Deletion Mutation in the 5' Part of the pol Gene of Moloney Murine Leukemia Virus Blocks Proteolytic Processing of the gag and pol Polyproteins", *J. Virol.*, 53, p. 899 (1985)). These gene products include pol, which encodes the virion RNA-dependent DNA polymerase (reverse transcriptase), an endonuclease, HIV protease, and gag, which encodes the core-proteins of the virion (H. Toh et al., "Close Structural Resemblance Between Putative Polymerase of a Drosophila Transposable Genetic Element 17.6 and pol gene product of Moloney Murine Leukemia Virus", *EMBO J.* 4, p. 1267 (1985); L. H. Pearl et al., "A Structural Model for the Retroviral Proteases", *Nature*, pp. 329–351 (1987); M. D. Power et al., "Nucleotide Sequence of SRV-1, a Type D Simian Acquired Immune Deficiency Syndrome Retrovirus", *Science*, 231, p. 1567 (1986)).

A number of synthetic anti-viral agents have been designed to target various stages in the replication cycle of HIV. These agents include compounds which block viral binding to $CD_4^+$ T-lymphocytes (for example, soluble CD4), and compounds which interfere with viral replication by inhibiting viral reverse transcriptase (for example, didanosine and zidovudine (AZT)) and inhibit integration of viral DNA into cellular DNA (M. S. Hirsh and R. T. D'Aquila, "Therapy for Human Immunodeficiency Virus Infection", *N. Eng. J. Med.*, 328, p. 1686 (1993)). However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, drug design efforts have been directed toward creating compounds which inhibit the formation of infectious virions by interfering with the processing of viral polyprotein precursors. Processing of these precursor proteins requires the action of virus-encoded proteases which are essential for replication (Kohl, N. E. et al. "Active HIV Protease is Required for Viral Infectivity" *Proc. Natl. Acad. Sci. USA*, 85, p. 4686 (1988)). The anti-viral potential of HIV protease inhibition has been demonstrated using peptidal inhibitors. Such peptidal compounds, however, are typically large and complex molecules that tend to exhibit poor bioavailability and are not generally consistent with oral administration. Accordingly, the need still exists for compounds that can effectively inhibit the action of viral proteases, for use as agents for preventing and treating chronic and acute viral infections. Such agents would be expected to act as effective therapeutic agents in their own right. In addition, since they act at a separate stage in the virus life cycle from previously described antiretroviral agents, the administration of a combination of agents would be expected to result in increased therapeutic efficacy.

SUMMARY OF THE INVENTION

The present invention provides a novel class of compounds, and pharmaceutically acceptable derivatives thereof, that are useful as inhibitors of aspartyl proteases, in particular, HIV aspartyl protease. These compounds can be used alone or in combination with other therapeutic or prophylactic agents, such as anti-virals, antibiotics, immunomodulators or vaccines, for the treatment or prophylaxis of viral infection.

According to a preferred embodiment, the compounds of this invention are capable of inhibiting HIV viral replication in human $CD_4^+$ cells including T-cells, monocytic lines including macrophages and dendrocytes and other permissive cells. These compounds are useful as therapeutic and prophylactic agents to treat or prevent infection by HIV-1 and related viruses which may result in asymptomatic infection, AIDS-related complex ("ARC"), acquired immunodeficiency syndrome ("AIDS"), or similar disease of the immune system.

It is a principal object of this invention to provide a class of THF-containing sulfonamides which are aspartyl protease inhibitors, and particularly, HIV aspartyl protease inhibitors. This class of THF-containing sulfonamides is represented by formula I:

$$\text{THF}-R^1-\text{NH}-\overset{\overset{\displaystyle D}{|}}{\text{CH}}-\overset{\overset{\displaystyle OH}{|}}{\text{CH}}-\text{CH}_2-\overset{\overset{\displaystyle D'}{|}}{\text{N}}-\text{SO}_2-E \qquad (I)$$

wherein:
  each $R^1$ is independently selected from the group consisting of —C(O)—, —S(O)$_2$—, —C(O)—C(O)—, —O—C(O)—, —O—S(O)$_2$, —NR$^2$S(O)$_2$—, —NR$^2$—C(O)— and —NR$^2$—C(O)—C(O)—;
  each Het is independently selected from the group consisting of $C_3$–$C_7$ carbocycle; $C_6$–$C_{10}$ aryl; phenyl fused with heterocycle; and heterocycle; wherein any member of said Het may be optionally substituted with one or more substituents selected from the group consisting of oxo, —OR$^2$, —R$^2$, —N(R$^2$)(R$^2$), —NHOH, —R$^2$—OH, —CN, —CO$_2$R$^2$, —C(O)—N(R$^2$)(R$^2$), —S(O)$_2$—N(R$^2$)(R$^2$), —N(R$^2$)—C(O)—R$^2$, —C(O)—R$^2$, —S(O)$_n$—R$^2$, —OCF$_3$, —S(O)$_n$—R$^6$, —N(R$^2$) S(O)$_2$(R$^2$), halo, —CF$_3$, —NO$_2$, —R$^6$ and —O—R$^6$;

each R$^2$ is independently selected from the group consisting of H and C$_1$–C$_3$ alkyl optionally substituted with R$^6$;

each R$^3$ is independently selected from the group consisting of H, Het, C$_1$–C$_6$ alkyl and C$_2$–C$_6$ alkenyl wherein any member of said R$^3$, except H, may be optionally substituted with one or more substituents selected from the group consisting of —OR$^2$, —C(O)—NH—R$^2$, —S(O)$_n$—N(R$^2$)(R$^2$), Het, —CN, —SR$^2$, —CO$_2$R$^2$, NR$^2$—C(O)—R$^2$;

each n is independently 1 or 2;

each D and D' is independently selected from the group consisting of R$^6$; C$_1$–C$_5$ alkyl, which may be optionally substituted with one or more groups selected from —OR$^2$, —R$^3$, —O—R$^6$, —S—R$^6$ and R$^6$; C$_2$–C$_4$ alkenyl, which may be optionally substituted with one or more groups selected from the group consisting of —OR$^2$, —R$^3$, —O—R$^6$ and R$^6$; and C$_3$–C$_6$ carbocycle, which may be optionally substituted with or fused with R$^6$;

each E is independently selected from the group consisting of Het; —O—Het; Het—Het; —O—R$^3$; —NR$^2$R$^3$; C$_1$–C$_6$ alkyl, which may be optionally substituted with one or more groups selected from the group consisting of R$^4$ and Het; and C$_2$–C$_6$ alkenyl, which may be optionally substituted with one or more groups selected from the group consisting of R$^4$ and Het;

each R$^4$ is independently selected from the group consisting of —OR$^2$, —C(O)—NHR$^2$, —S(O)$_2$—NHR$^2$, halo, —NR$^2$—C(O)—R$^2$ and —CN; and each R$^5$ is independently selected from the group consisting of H and C$_1$–C$_4$ alkyl optionally substituted with aryl; and each R$^6$ is independently selected from the group consisting of aryl, carbocycle and heterocycle, wherein said aryl, carbocycle or heterocycle may be optionally substituted with one or more groups selected from the group consisting of oxo, —OR$^5$, —R$^5$, —N(R$^5$)(R$^5$), —N(R$^5$)—C(O)—R$^5$, —R$^5$—OH, —CN, —CO$_2$R$^5$, —C(O)—N(R$^5$)(R$^5$), halo and —CF$_3$.

It is also an object of this invention to provide pharmaceutical compositions comprising the THF-containing sulfonamides of formula I and methods for their use as inhibitors of HIV aspartyl protease.

DETAILED DESCRIPTION OF THE INVENTION

In order that the invention herein described may be more fully understood, the following detailed description is set forth. In the description, the following abbreviations are used:

| Designation | Reagent or Fragment |
|---|---|
| Ac | acetyl |
| Me | methyl |
| Et | ethyl |
| Bn | benzyl |
| Trityl | triphenylmethyl |
| Asn | D- or L-asparagine |
| Ile | D- or L-isoleucine |
| Phe | D- or L-phenylalanine |
| Val | D- or L-valine |
| Boc | tert-butoxycarbonyl |
| Cbz | benzyloxycarbonyl (carbobenzyloxy) |
| DCC | dicyclohexylcarbodiimide |
| DBU | 1,8-diazabicyclo(5.4.0)undec-7-ene |
| DIC | diisopropylcarbodiimide |
| DIEA | diisopropylethylamine |

| Designation | Reagent or Fragment |
|---|---|
| DMF | dimethylformamide |
| DMSO | dimethylsulfoxide |
| EDC | 1-(3-dimethylaminopropyl)-3-ethylcarbodiimide hydrochloride |
| EtOAc | ethyl acetate |
| Fmoc | 9-fluorenylmethoxycarbonyl |
| HOBt | 1-hydroxybenzotriazole |
| HOSu | 1-hydroxysuccinimide |
| iBu | iso-butyl |
| NCA | N-carboxyanhydride |
| t-Bu | tert-butyl |
| TFA | trifluoroacetic acid |
| THP | tetrahydropyran |
| THF | tetrahydrofuran |
| TMSCl | chlorotrimethylsilane |

The following terms are employed herein:

Unless expressly stated to the contrary, the terms "—SO$_2$—" and "—S(O)$_2$—" as used herein refer to a sulfone or sulfone derivative (i.e., both appended groups linked to the S), and not a sulfinate ester.

The term "backbone" refers to the structural representation of a compound of this invention, as set forth in the figures drawn in this application. The term "backbone" does not encompass the variables drawn in those figures.

For the compounds of formula I, and intermediates thereof, the stereochemistry of the explicitly shown hydroxyl is defined relative to D on the adjacent carbon atom, when the molecule is drawn in an extended zig-zag representation (such as that drawn for compounds of formula VI). If both OH and D reside on the same side of the plane defined by the extended backbone of the compound, the stereochemistry of the hydroxyl will be referred to as "syn". If OH and D reside on opposite sides of that plane, the stereochemistry of the hydroxyl will be referred to as "anti".

As used herein, the term "alkyl", alone or in combination with any other term, refers to a straight-chain or branch-chain saturated aliphatic hydrocarbon radical containing the specified number of carbon atoms, or where no number is specified, preferably from 1–10 and more preferably from 1–5 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, preferably from 2–10 carbon atoms and more preferably, from 2–6 carbon atoms. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "aryl", alone or in combination with any other term, refers to a carbocyclic aromatic radical (such as phenyl or naphthyl) containing the specified number of carbon atoms, preferably from 6–14 carbon atoms, and more preferably from 6–10 carbon atoms. Examples of aryl radicals include, but are not limited to phenyl, naphthyl, indenyl, indanyl, azulenyl, fluorenyl, anthracenyl and the like.

The term "cycloalkyl", alone or in combination with any other term, refers to a cyclic saturated hydrocarbon radical containing the specified number of carbon atoms, preferably from 3–7 carbon atoms. Examples of cycloalkyl radicals include, but are not limited to, cyclopropyl, cyclobutyl, cyclopentyl, cyclohexyl, cycloheptyl and the like.

The term "cycloalkenyl", alone or in combination with any other term, refers to a cyclic hydrocarbon radical containing the specified number of carbon atoms with at least one endocyclic carbon—carbon bond. Where no number of carbon atoms is specified, a cycloalkenyl radical preferably has from 5–7 carbon atoms. Examples of cycloalkenyl radicals include, but are not limited to, cyclopentenyl, cyclohexenyl, cyclopentadienyl and the like.

The term "THF" refers to a tetrahydrofuran ring attached at any ring carbon resulting in a stable structure, but preferably attached at the 3-position of the tetrahydrofuran ring (i.e., tetrahydrofuran-3-yl). Preferably, the chiral carbon of THF is in the (S) configuration.

The term "carbocycle" refers to a stable non-aromatic 3- to 8-membered carbon ring radical which may be saturated, mono-unsaturated or poly-unsaturated. The carbocycle may be attached at any endocyclic carbon atom which results in a stable structure. Preferred carbocycles have 5–6 carbons. Examples of carbocycle radicals include, but are not limited to, cyclopropyl, cyclobutyl, cyclopentyl, cyclohexyl, cycloheptyl, cyclopentenyl, cyclohexenyl, cyclopentadienyl and the like.

The term "heterocycle", unless otherwise defined herein, refers to a stable 3–7 membered monocyclic heterocyclic ring or 8–11 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. In addition, any ring nitrogen may be optionally substituted with a substituent $R^2$, as defined herein for compounds of formula I. A heterocycle may be attached at any endocyclic carbon or heteroatom which results in the creation of a stable structure. A heterocycle may be attached at any endocyclic carbon or heteroatom which results in the creation of a stable structure. Preferred heterocycles include 5–7 membered monocyclic heterocycles and 8–10 membered bicyclic heterocycles. Preferred heterocycles defined above include, for example, benzimidazolyl, imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, oxazolyl, benzoxazolyl, oxopiperidinyl, oxopyrroldinyl, oxoazepinyl, azepinyl, isoxazolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, dioxanyl, dioxolanyl, tetrahydrofurotetrahydrofuranyl, tetrahydropyranotetrahydrofuranyl, tetrahydrofurodihydrofuranyl, tetrahydropyranodihydrofuranyl, dihydropyranyl, dihydrofuranyl, dihydrofurotetrahydrofuranyl, dihydropyranotetrahydrofuranyl, sulfolanyl and the like.

The term "halo" refers to a radical of fluorine, chlorine, bromine or iodine.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "anti-viral agent" or "anti-retroviral agent" refers to a compound or drug which possesses viral inhibitory activity. Such agents include reverse transcriptase inhibitors (including nucleoside and non-nucleoside analogs) and protease inhibitors. Preferably the protease inhibitor is an HIV protease inhibitor. Examples of nucleoside analog reverse transcriptase inhibitors include, but are not limited to, zidovudine (AZT), dideoxycytidine (ddC), didanosine (ddI), stavudine (d4T), 3TC, 935U83, 1592U89 and 524W91. Examples of non-nucleoside analog reverse transcriptase inhibitors include, but are not limited to delavirdine (U90) and nevirapine. Examples of HIV protease inhibitors include, but are not limited to, saquinavir (Ro 31-8959), MK 639, ABT 538 (A80538), AG 1343, XM 412, XM 450, BMS 186318 and CPG 53,437.

The term "leaving group" or "LG" refers to groups readily displaceable by a nucleophile, such as an amine, alcohol, phosphorous or thiol nucleophile or their respective anions. Such leaving groups are well known and include carboxylates, N-hydroxysuccinimide, N-hydroxybenzotriazole, halogen (halides), triflates, tosylates, mesylates, alkoxy, thioalkoxy, phosphinates, phosphonates and the like. Other potential nucleophiles include organometallic reagents known to those skilled in the art. In addition, the term "leaving group" or "LG" is meant to encompass leaving group precursors (i.e., moieties that can be easily converted to a leaving group upon simple synthetic procedures such as alkylation, oxidation or protonation). Such leaving group precursors and methods for converting them to leaving groups are well known to those of ordinary skill in the art. Leaving group precursors include, for instance, secondary and tertiary amines. By way of example, the moiety —N($R_3$)($R_4$), while not itself a leaving group, is encompassed by the term "leaving group" or "LG" because it can be readily converted to a leaving group such as —$N^+CH_3(R_3)(R_4)$.

The term "protecting group" refers to a suitable chemical group which may be attached to a functional group and removed at a later stage to reveal the intact functional group. Examples of suitable protecting groups for various functional groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995).

The term "silyl" refers to a trisubstituted silicon radical in which the substituents are independently $C_1$–$C_8$ alkyl, $C_5$–$C_7$ aryl or $C_5$–$C_7$ carbocycle. Examples of silyl include, but are not limited to, trimethylsilyl, triethylsilyl, triisopropylsilyl, t-butyldimethylsilyl, t-butyldiisopropylsilyl, t-butyldiphenylsilyl, triphenylsilyl, cyclohexyldimethylsilyl and the like.

The term "pharmaceutically effective amount" refers to an amount effective in treating HIV infection in a patient either as monotherapy or in combination with other agents. The term "treating" as used herein refers to the alleviation of symptoms of a particular disorder in a patient or the improvement of an ascertainable measurement associated with a particular disorder. Specifically, with respect to HIV, effective treatment using the compounds and compositions of this invention would result in an improvement in an HIV associated ascertainable measurement. Such measurements include, but are not limited to, reduction in viral load in plasma or another defined tissue compartment as measured by, e.g. RT-PCR or branched-chain DNA PCR or culturable virus measurements, β-2 microglobulin or p24 levels, number of $CD_4^+$ cells or ratio of $CD_4^+/CD_8^+$ cells, or functional markers such as improvement in quality of life, ability to carry out normal functions, reduction of dementia or immunosuppression-related effects including, but not limited to, opportunistic infections and tumors. The term "prophylactically effective amount" refers to an amount effective in preventing HIV infection in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in uses sufficient to deliver a therapeutic amount of the antiretroviral agent.

The term "point of attachment" refers to the atom through which a moiety is attached to a specified structure.

The term "substituted", whether express or implied and whether preceded by the term "optionally" or not, refers to the replacement of one or more hydrogen radicals in a given structure with the radical of a specified substituent. When more than one position in a given structure may be substituted with a substituent selected from a specified group, the substituents may be either the same or different at every position. Typically, when a structure may be optionally substituted, 0–3 substitutions are preferred, and 0–1 substitution is most preferred. Most preferred substituents are those which enhance protease inhibitory activity or intracellular antiviral activity in permissive mammalian cells or immortalized mammalian cell lines, or which enhance deliverability by enhancing solubility characteristics or enhancing pharmacokinetic or pharmacodynamic profiles as compared to the unsubstituted compound. Other most preferred substituents include those used in the compounds shown in Table I.

As used herein, the compounds of this invention, including the compounds of formula I, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the explicitly shown hydroxyl in formula (I) or to "E" in formula (I).

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, p-toluenesulfonic, tartaric, acetic, citric, methanesulfonic, ethanesulfonic, formic, benzoic, malonic, naphthalene-2-sulfonic and benzenesulfonic acids. Preferred acids include hydrochloric, sulfuric, methanesulfonic and ethanesulfonic acids. Methanesulfonic acid is most preferred. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and $N-(C_{1-4}\ alkyl)_4^+$ salts.

The term "thiocarbamates" refers to compounds containing the functional group $N—SO_2—O$.

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. The explicitly shown hydroxyl is also preferred to be syn to D, in the extended zig-zag conformation between the nitrogens shown in compounds of formula I.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

The compounds of the present invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate and undecanoate.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The THF-containing sulfonamides of this invention are those of formula I:

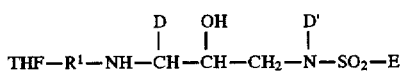

$$\text{THF}-R^1-NH-\overset{\overset{D}{|}}{CH}-\overset{\overset{OH}{|}}{CH}-CH_2-\overset{\overset{D'}{|}}{N}-SO_2-E \qquad (I)$$

wherein:

each $R^1$ is independently selected from the group consisting of —C(O)—, —S(O)$_2$—, —(O)—C(O)—, —O—C(O)—, —O—S(O)$_2$, —NR$^2$—S(O)$_2$—, —NR$_2$—C(O)— and —NR$_2$—C(O)—C(O)—; preferably each $R^1$ is —O—C(O)— or —C(O)—; more preferably each $R^1$ is —O—C(O)—;

each Het is independently selected from the group consisting of $C_3$–$C_7$ carbocycle; $C_6$–$C_{10}$ aryl; phenyl fused with heterocycle; and heterocycle; wherein any member of said Het may be optionally substituted with one or more substituents selected from the group consisting of oxo, —OR$^2$, —R$^2$, —N(R$^2$)(R$^2$), —NHOH, —R$^2$—OH, —CN, —CO$_2$R$^2$, —C(O)—N(R$^2$)(R$^2$), —S(O)$_2$—N(R$^2$)(R$^2$), —N(R$^2$)—C(O)—R$^2$, —C(O)—R$^2$, —S(O)$_n$—R$^2$, —OCF$_3$, —S(O)$_n$—R$^6$, —N(R$^2$)—S(O)$_2$(R$^2$), halo, —CF$_3$, —NO$_2$, —R$^6$ and —O—R$^6$;

each $R^2$ is independently selected from the group consisting of H and $C_1$–$C_3$ alkyl optionally substituted with $R^6$;

each $R^3$ is independently selected from the group consisting of H, Het, $C_1$–$C_6$ alkyl and $C_2$–$C_6$ alkenyl wherein any member of said $R^3$, except H, may be optionally substituted with one or more substituents selected from the group consisting of —OR$^2$, —C(O)—NH—R$^2$, —S(O)$_n$—N(R$^2$)(R$^2$), Het, —CN, —SR$^2$, —CO$_2$R$^2$, NR$^2$—C(O)—R$^2$;

each n is independently 1 or 2;

each D and D' is independently selected from the group consisting of $R^6$; $C_1$–$C_6$ alkyl, which may be optionally substituted with one or more groups selected from —OR$^2$, —R$^3$, —O—R$^6$ and R$^6$; $C_2$–$C_4$ alkenyl, which may be optionally substituted with one or more groups selected from the group consisting of —OR$^2$, —R$^3$, —O—R$^6$ and R$^6$; $C_{3-C6}$ carbocycle, which may be optionally substituted with or fused with $R^6$; and $C_5$–$C_6$ cycloalkenyl, which may be optionally substituted with or fused with $R^6$; preferably each D is independently $C_1$–$C_5$ alkyl, which may be optionally substituted with one or more Het; more preferably D is $C_1$–$C_5$ alkyl, which may be optionally substituted with one group selected from $C_6$–$C_{10}$ aryl and $C_3$–$C_6$ cycloalkyl; even more preferably D is selected from benzyl, isobutyl, cyclopentylmethyl, and cyclohexylmethyl; and most preferably, D is benzyl or isobutyl; preferably each D' is independently selected from the group consisting of $C_1$–$C_6$ alkyl optionally substituted with $R^6$; and more preferably D' is selected from the group consisting of $C_1$–$C_4$ alkyl optionally substituted with one 3–6 membered carbocycle or one 5–6 membered heterocycle; and most preferably, D' is selected from the group consisting of isobutyl, cyclopentylmethyl and cyclohexylmethyl;

each E is independently selected from the group consisting of Het; —O—Het; Het—Het; —O—R$^3$; —NR$^2$R$^3$; $C_1$–$C_6$ alkyl, which may be optionally substituted with one or more groups selected from the group consisting of R$^4$ and Het; $C_2$–$C_6$ alkenyl, which may be optionally substituted with one or more groups selected from the group consisting of R$^4$ and Het; and phenyl fused with 5–6 membered heterocycle; preferably each E is Het and more preferably, E is phenyl substituted with one or more substituents selected from the group consisting of —OH, —OCH$_3$, —NH$_2$, —NHCOCH$_3$, —SH, and —CH$_3$; or phenyl fused with 5–6 membered heterocycle, and most preferably, E is phenyl substituted with —NH$_2$ (preferably in the meta- or para- position);

each $R^4$ is independently selected from the group consisting of —OR$^2$, —C(O)—NHR$^2$, —S(O)NHR$^2$, halo, —NR$^2$—C(O)—R$^2$ and —CN;

each $R^5$ is independently selected from the group consisting of H and $C_1$–$C_4$ alkyl optionally substituted with aryl; preferably each $R^5$ is independently selected from the group consisting of H and $C_1$–$C_3$ alkyl; and each $R^6$ is independently selected from the group consisting of aryl, carbocycle and heterocycle, wherein said carbocycle or heterocycle may be optionally substituted with one or more groups selected from the group consisting of oxo, —OR$^5$, —R$^5$, —N(R$^5$)(R$^5$), —N(R$^5$)—C(O)—R$^5$, —R$^5$—OH, —CN, —CO$_2$R$^5$, —C(O)—N(R$^5$)(R$^5$), halo and —CF$_3$; preferably each $R^6$ is independently selected from the group consisting of 3–6 membered carbocycle and 5–6 membered heterocycle, wherein said heterocycle or carbocycle may be optionally substituted with one or more groups selected from the group consisting of oxo, —OR$^5$, —R$^5$, —N(R$^5$)(R$^5$), —N(R$^5$)—C(O)—R$^5$, —R$^5$—OH, —CN, —CO$_2$R$^5$, —C(O)—N(R$^5$)(R$^5$), halo and —CF$_3$.

Except where expressly noted to the contrary, the term "[variable] as defined for formula I" refers to the definitions shown directly above.

Preferred compounds of formula I include those compounds having at least one variable defined as the preferred, more preferred, even more preferred or most preferred definition above. More preferred compounds of formula I include those compounds having at least two to three variables defined independently as the preferred, more preferred, even more preferred or most preferred definitions above. Most preferred compounds of formula I include those compounds having at least four to five variables independently defined as the preferred, more preferred, even more preferred or most preferred definitions above.

Table I illustrates preferred compounds of this invention:

| # | THF | OH | D | D' | E |
|---|---|---|---|---|---|
| 35 | S | syn | —CH$_2$—C$_6$H$_5$ | —CH$_2$—CH(CH$_3$)$_2$ | C$_6$H$_4$—F |

-continued

Structural formula: tetrahydrofuran-3-yl O-C(=O)-NH-CH(D)-CH(OH)-CH₂-N(D')-SO₂-E

| # | THF | OH | D | D' | E |
|---|-----|-----|---|-----|---|
| 37 | S | syn | —CH₂—C₆H₅ | —CH₂—CH(CH₃)₂ | 3,4-dichlorophenyl |
| 48 | S | syn | —CH₂—C₆H₅ | —CH₂—CH(CH₃)₂ | 4-(NHCOCH₃)phenyl |
| 51 | S | syn | —CH₂—C₆H₅ | —CH₂—CH(CH₃)₂ | 5-(pyridin-2-yl)thiophen-2-yl |
| 52 | R,S | syn | —CH₂—C₆H₅ | —CH₂—CH(CH₃)₂ | 4-fluorophenyl |
| 53 | S | syn | —CH₂—C₆H₅ | —CH₂—CH(CH₃)₂ | 2-chloro-4-(NHCOCH₃)phenyl |
| 60 | S | syn | —CH₂—C₆H₅ | —CH₂—CH(CH₃)₂ | benzo[c][1,2,5]oxadiazol-4-yl |
| 66 | S | syn | —CH₂—C₆H₅ | —CH₂—CH(CH₃)₂ | benzo[c][1,2,5]oxadiazol-5-yl |
| 69 | S | syn | —CH₂—C₆H₅ | —CH₂—CH(CH₃)₂ | —N(CH₃)₂ |
| 86 | R,S | syn | —CH₂—C₆H₅ | —CH₂—CH(CH₃)₂ | 4-(NHCOCH₃)phenyl |
| 88 | S | syn | —CH₂—C₆H₅ | —CH₂—CH(CH₃)₂ | 2-fluoro-5-(NHCOCH₃)phenyl |

-continued

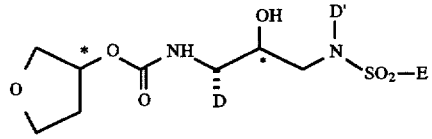

| # | THF | OH | D | D' | E |
|---|---|---|---|---|---|
| 91 | S | syn | —CH₂—C₆H₅ | —CH₂—CH(CH₃)₂ | 3-NHCOCH₃-C₆H₄— |
| 93 | R | syn | —CH₂—C₆H₅ | —CH₂—CH(CH₃)₂ | 4-F-C₆H₄— |
| 94 | R | syn | —CH₂—C₆H₅ | —CH₂—CH(CH₃)₂ | 4-NHCOCH₃-C₆H₄— |
| 95 | S | syn | —CH₂—C₆H₅ | —CH₂—CH(CH₃)₂ | 2,3-dichlorothien-5-yl |
| 99 | S | syn | —CH₂—C₆H₅ | —CH₂—CH(CH₃)₂ | 4-Cl-C₆H₄— |
| 100 | S | syn | —CH₂—C₆H₅ | —CH₂—CH(CH₃)₂ | 4-OCH₃-C₆H₄— |
| 101 | S | syn | —CH₂—C₆H₅ | CH₃ | 4-NHCOCH₃-C₆H₄— |
| 112 | S | syn | —CH₂—C₆H₅ | —CH₂—CH(CH₃)₂ | 3-SO₂NH₂-C₆H₄— |
| 113 | S | syn | —CH₂—C₆H₅ | —CH₂—CH(CH₃)₂ | furan-2-yl |
| 116 | S | syn | —CH₂—C₆H₅ | —CH₂-cyclopentyl | 4-Cl-C₆H₄— |
| 123 | S | syn | —CH₂—C₆H₅ | —CH₂—CH(CH₃)₂ | 3,4-(OCH₃)₂-C₆H₃— |
| 124 | S | syn | —CH₂—C₆H₅ | —CH₂—CH(CH₃)₂ | 3,4-F₂-C₆H₃— |

-continued

Structure: tetrahydrofuran-3-yl-O-C(=O)-NH-CH(D)-CH(OH)-CH2-N(D')-SO2-E

| # | THF | OH | D | D' | E |
|---|---|---|---|---|---|
| 125 | S | syn | —CH2—phenyl | —CH2—cyclopentyl | 4-NHCOCH3—phenyl |
| 132 | S | syn | —CH2—phenyl | —CH2—(tetrahydrofuran-2-yl) | 4-F—phenyl |
| 133 | S | syn | —CH2—phenyl | —CH2—(tetrahydrofuran-2-yl) | 4-NHCOCH3—phenyl |
| 134 | S | syn | —CH2—phenyl | —C(=CH2)—CH(CH3) (isopropenyl-like) | 4-NHCOCH3—phenyl |
| 135 | S | syn | —CH2—phenyl | —C(=CH2)—CH(CH3) | 4-F—phenyl |
| 136 | S | syn | —CH2—phenyl | —CH2—(furan-2-yl) | 4-F—phenyl |
| 137 | S | syn | —CH2—phenyl | —CH2—(furan-2-yl) | 4-NHCOCH3—phenyl |
| 138 | S | syn | —CH2—phenyl | —CH2—CH(CH3)2 | 3-Cl—phenyl |
| 140 | S | syn | —CH2—phenyl | —CH2—cyclopentyl | 4-OCH3—phenyl |
| 144 | S | syn | —CH2—phenyl | —CH2—CH(CH3)2 | pyridinium, CF3COO− H |
| 145 | S | syn | —CH2—phenyl | —CH2—CH(CH3)2 | methyl-thiophene-isoxazole |
| 148 | S | syn | —CH2—phenyl | —CH2—cyclopentyl | phenyl |

-continued

| # | THF | OH | D | D' | E |
|---|-----|-----|---|-----|---|
| 149 | S | syn | —CH₂—(phenyl) | —CH₂—(cyclopentyl) | (3-pyridyl) |
| 150 | S | syn | —CH₂—(phenyl) | —CH₂—CH(CH₃)₂ | —N(piperidinyl) |
| 151 | S | syn | —CH₂—(phenyl) | —CH₂—(cyclopentyl) | (4-OCF₃-phenyl) |
| 152 | S | syn | —CH₂—(phenyl) | —CH₂—CH(CH₃)₂ | (4-OCF₃-phenyl) |
| 157 | S | syn | —CH₂—(phenyl) | —CH₂—(cyclopentyl) | (5-methyl-indolinyl-N-COCH₃) |
| 158 | S | syn | —CH₂—(phenyl) | —CH₂—(cyclohexyl) | (4-OCH₃-phenyl) |
| 159 | S | syn | —CH₂—(phenyl) | —CH₂—(cyclohexyl) | (4-F-phenyl) |
| 160 | S | syn | —CH₂—(phenyl) | —CH₂—(cyclohexyl) | (4-NHCOCH₃-phenyl) |
| 161 | S | syn | —CH₂—(phenyl) | —CH₂—CH(CH₃)₂ | —N(morpholinyl) |
| 165 | S | syn | —CH₂—(phenyl) | —CH₂—CH(CH₃)₂ | (4-CH₃-phenyl) |
| 167 | S | syn | —CH₂—(phenyl) | —CH₂—CH(CH₃)₂ | (4-NO₂-phenyl) |
| 168 | S | syn | —CH₂—(phenyl) | —CH₂—CH(CH₃)₂ | (4-NH₂-phenyl) |
| 169 | S | syn | —CH₂—(phenyl) | —CH₂—(cyclopentyl) | (4-OH-phenyl) |

-continued

[Structure: tetrahydrofuran-3-yl-O-C(=O)-NH-CH(D)-CH(OH)-CH2-N(D')-SO2-E]

| # | THF | OH | D | D' | E |
|---|-----|----|----|----|----|
| 170 | S | syn | −CH2−phenyl | −CH2−cyclopentyl | 4-NO2-phenyl |
| 171 | S | syn | −CH2−phenyl | −CH2−cyclopentyl | 4-NH2-phenyl |
| 172 | S | syn | −CH2−phenyl | −CH2−cyclopentyl | 2,4-dinitrophenyl |
| 173 | S | syn | −CH2−phenyl | −CH2−cyclopentyl | 2,4-diaminophenyl |
| 174 | S | syn | −CH2−phenyl | −CH2−CH(CH3)2 | 4-(benzyloxy)phenyl |
| 175 | S | syn | −CH2−phenyl | −CH2−CH(CH3)2 | 4-OH-phenyl |
| 176 | S | syn | −CH2−phenyl | −CH2−cyclopentyl | 3,4-methylenedioxyphenyl |
| 180 | S | syn | −CH2−phenyl | −CH2−cyclopentyl | 2,3-dihydrobenzofuran-5-yl |
| 181 | S | syn | −CH2−phenyl | −CH2−cyclopentyl | 4-CN-phenyl |
| 182 | S | syn | −CH2−phenyl | −CH2−cyclopentyl | 4-F-phenyl |

-continued

| # | THF | OH | D | D' | E |
|---|---|---|---|---|---|
| 183 | S | syn | —CH₂-phenyl | —CH₂-cyclopentyl | 3,4-dichlorophenyl |
| 195 | S | syn | —CH₂-cyclohexyl | —CH₂-cyclopentyl | 4-OCH₃-phenyl |
| 196 | S | syn | —CH₂-CH(CH₃)₂ | —CH₂-CH(CH₃)₂ | 4-OCH₃-phenyl |
| 197 | S | syn | —CH₂-phenyl | —CH₂-CH(CH₃)₂ | 4-SCH₃-phenyl |
| 198 | S | syn | —CH₂-phenyl | —CH₂-cyclopentyl | 4-SCH₃-phenyl |
| 199 | S | syn | —CH₂-CH(CH₃)₂ | —CH₂-CH(CH₃)₂ | 4-OCH₃-phenyl |
| 200 | S | syn | —CH₂-phenyl | —CH₂-cyclopentyl | 4-N(CH₃)₂-phenyl |
| 201 | S | syn | —CH₂-phenyl | —CH₂-CH(CH₃)₂ | 4-N(CH₃)₂-phenyl |
| 202 | S | syn | —CH₂-phenyl | —CH₂-cyclopentyl | 4-OEt-phenyl |
| 203 | S | syn | —CH₂-CH(CH₃)₂ | —CH₂-cyclopentyl | 4-OCH₃-phenyl |
| 204 | S | syn | —CH₂-CH(CH₃)₂ | —CH₂-cyclopentyl | 4-OCH₃-phenyl |
| 205 | S | syn | —CH₂-CH(CH₃)₂ | —CH₂-cyclopentyl | 4-NO₂-phenyl |
| 206 | S | syn | —CH₂-CH(CH₃)₂ | —CH₂-cyclopentyl | 4-OH-phenyl |

-continued

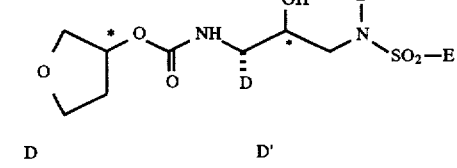

| # | THF | OH | D | D' | E |
|---|---|---|---|---|---|
| 207 | S | anti | isobutyl (–CH₂CH(CH₃)₂) | –CH₂-cyclopentyl | 4-hydroxyphenyl |
| 208 | S | syn | isobutyl | –CH₂-cyclopentyl | 4-aminophenyl |
| 209 | S | syn | –CH₂-phenyl | –CH₂-cyclopentyl | 4-(methylsulfonyl)phenyl |
| 210 | S | syn | –CH₂-phenyl | isobutyl | 4-(methylsulfonyl)phenyl |
| 211 | S | syn | –CH₂-phenyl | –CH₂-cyclopentyl | 4-(CO₂CH₃)phenyl |
| 212 | S | syn | isobutyl | –CH₂-cyclohexyl | 4-hydroxyphenyl |
| 213 | S | syn | isobutyl | –(CH₂)₂-phenyl | 4-hydroxyphenyl |
| 214 | S | syn | isobutyl | –(CH₂)₂-phenyl | 4-aminophenyl |
| 215 | S | syn | isobutyl | –CH₂-cyclohexyl | 4-aminophenyl |
| 216 | S | syn | –CH₂-phenyl | –CH₂-cyclopentyl | 3-aminophenyl |
| 217 | S | syn | –CH₂-phenyl | isobutyl | 3-aminophenyl |
| 218 | S | syn | –CH₂-phenyl | –CH₂-cyclopentyl | 3-nitro-4-methoxyphenyl |

-continued

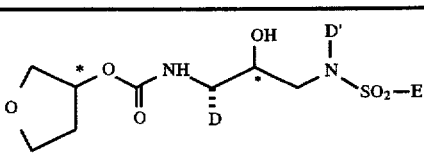

| # | THF | OH | D | D' | E |
|---|---|---|---|---|---|
| 219 | S | syn | —CH₂—C₆H₅ | —CH₂-cyclopentyl | 2-amino-4-methoxyphenyl (NH₂, OCH₃) |
| 220 | S | syn | —CH₂—C₆H₅ | —CH₂CH(CH₃)₂ | 2-amino-4-hydroxyphenyl (NH₂, OH) |
| 221 | S | syn | —CH₂—C₆H₅ | —CH₂CH(CH₃)₂ | 4-(N(H)OH)phenyl |
| 222 | S | syn | —CH₂—C₆H₅ | —CH₂CH(CH₃)₂ | phenyl |
| 223 | S | syn | —CH₂—C₆H₅ | —(CH₂)₂—N(pyrrolidinyl) | 4-OCH₃-phenyl |
| 224 | S | syn | —CH₂—C₆H₅ | —CH₂-cyclopentyl | 4-OCH₃-phenyl |
| 225 | S | syn | —CH₂—C₆H₅ | —CH₂-(4-piperidinyl, N—H) | 4-OCH₃-phenyl |
| 226 | S | syn | —CH₂—C₆H₅ | —CH₂-(4-piperidinyl, N—CH₃) | 4-OCH₃-phenyl |
| 227 | S | syn | —CH₂—C₆H₅ | —CH₂-(4-piperidinyl, N—COCH₃) | 4-OCH₃-phenyl |
| 228 | S | syn | —CH₂—C₆H₅ | 4-piperidinyl (N—H) | 4-OCH₃-phenyl |
| 229 | S | syn | —CH₂—C₆H₅ | 4-piperidinyl (N—COCH₃) | 4-OCH₃-phenyl |
| 230 | S | syn | —CH₂—C₆H₅ | —(CH₂)₂—N(piperidinyl) | 4-OCH₃-phenyl |

-continued

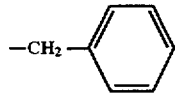

| # | THF | OH | D | D' | E |
|---|-----|-----|---|-----|---|
| 231 | S | syn | —CH₂—⟨phenyl⟩ | —⟨piperidinyl⟩N—CH₃ | —⟨phenyl⟩—OCH₃ |
| 232 | S | syn | —CH₂—⟨phenyl⟩ | —CH₂—C(CH₃)(CH₃)—OH | —⟨phenyl⟩—OCH₃ |
| 233 | S | syn | —CH₂—⟨phenyl⟩ | —CH₂—C(CH₃)(CH₃)—CH₂OH | —⟨phenyl⟩—OCH₃ |
| 234 | S | syn | —CH₂—⟨phenyl⟩ | thiazolyl | —⟨phenyl⟩—OCH₃ |
| 235 | S | syn | —CH₂—⟨phenyl⟩ | —N(tetrazolyl) | —⟨phenyl⟩—OCH₃ |
| 236 | S | syn | —CH₂—⟨phenyl⟩ | —CH₂—⟨cyclopentyl⟩ | —CH₂—⟨phenyl⟩ |

More preferred compounds of this invention are selected from the group consisting of compound 35; compound 37; compound 48; compounds 52; compound 60; compound 66; compounds 86; compound 88; compound 91; compound 93; compound 94; compound 95; compound 99; compound 100; compound 112; compound 113; compound 116; compound 124; compound 125; compound 132; compound 134; compound 135; compound 138; compound 140; compound 144; compound 145; compound 148; compound 149; compound 150; compound 151; compound 152; compound 157; compound 158; compound 159; compound 160; compound 165; compound 167; compound 168; compound 169; compound 170; compound 171; compound 173; compound 175; compound 176; compound 180; compound 181; compound 182; compound 183; compound 195; compound 196; compound 197; compound 198; compound 200; compound 201; compound 202; compound 203; compound 204; compound 205; compound 206; compound 208; compound 209; compound 210; compound 211; compound 212; compound 213; compound 216; compound 217; compound 218; compound 219; compound 220; compound 221; compound 222; compound 224; compound 227; and compound 233, wherein each compound has the formula shown in Table I.

Even more preferred compounds of this invention are selected from the group consisting of: compound 48; compound 100; compound 116, compound 140; compound 148; compound 158; compound 160; compound 168; compound 169; compound 171; compound 173; compound 175; compound 176; compound 180; compound 181; compound 195; compound 197; compound 198; compound 202; compound 206; compound 211; compound 216; compound 217; compound 219 and compound 220, wherein each compound has the formula shown in Table I.

The most preferred compounds of this invention are selected from the group consisting of: compound 140; compound 168; compound 169; compound 171; compound 175; compound 216; and compound 217, wherein each compound has the formula shown in Table I.

The THF-containing sulfonamides of this invention may be synthesized using conventional techniques. Advantageously, these compounds may be conveniently synthesized from readily available starting materials.

The compounds of this invention are among the most readily synthesized HIV protease inhibitors known. Previously described HIV protease inhibitors often contain four or more chiral centers, numerous peptide linkages and/or require air-sensitive reagents (such as organometallic complexes) to effect their synthesis. The relative ease with which the compounds of this invention can be synthesized represents an enormous advantage in the large scale production of these compounds.

In general, the THF-containing sulfonamides of this invention are conveniently obtained from α-amino acids and derivatives thereof having the general formula II:

(W)(Q)N—CH(D)—Y    (II)

wherein W is hydrogen or P; P is a suitable amino protecting group; Q is hydrogen, benzyl or A—R¹—; Y is —C(O)OH, —C(O)H, or —CH₂OH; and D and A—R¹— are as defined above for the compounds of formula I. W and Q may also be taken together with the nitrogen to which they are attached to form a heterocycle. An example of such a construction is phthalimide. Suitable amino protecting groups are described in numerous references, including T. W. Greene and P. G. M. Wuts, *Protective Groups in Organic Synthesis*, 2d Ed., John Wiley and Sons (1991); L. Fieser and M. Fieser, *Fieser and Fieser's Reagents for Organic Synthesis*, John Wiley and Sons (1994); and L. Paquette, ed. *Encyclopedia of Reagents for Organic Synthesis*, John Wiley and Sons (1995). Examples of such amino protecting groups include, but are not limited to, Boc, Cbz and Alloc. Alternatively, the amine may be protected as an alkyl derivative such as N,N-dibenzyl or trityl. Such α-amino acid derivatives are often commercially available or may be conveniently prepared from commercially available α-amino acid derivatives using known techniques. Although this invention envisions the use of racemic mixtures of such starting materials, a single enantiomer (preferably in the S configuration) is preferred.

Using known techniques, the α-amino acid derivative of general formula P—N(Q)—CH(D)—COOH may be readily converted to an amino ketone derivative of general formula P—N(Q)—CH(D)—CO—CH$_2$—X, wherein P, Q and D are as defined for compounds of formula II and X is a leaving group which suitably activates the α-carbon (i.e., increases the susceptibility of the methylene to nucleophilic attack). Suitable leaving groups are well known in the art and include halides, dialkyl sulfonium salts and sulfonates, such as methanesulfonate, trifluoromethanesulfonate or 4-toluenesulfonate. X may also be a hydroxyl which is converted in situ to a leaving group (e.g., by treatment with a trialkyl- or triarylphosphine in the presence of a dialkylazodicarboxylate). Methods for the formation of such amino ketone derivatives also are well known to those of skill in the art (see, for example, S. J. Fittkau, *J. Prakt. Chem.*, 315, p. 1037 (1973)). In addition, certain amino ketone derivatives are commercially available (e.g., from Bachem Biosciences, Inc., Philadelphia, Pa.).

The amino ketone derivative may then be reduced to the corresponding amino alcohol, represented by the formula P—N(Q)—CH(D)—CH(OH)—CH$_2$—X, wherein P, Q and D are as defined above for compounds of formula II and X is a leaving group as defined above. Alternatively, the amino ketone derivative can be reduced to the corresponding alcohol later in the synthetic scheme. Many techniques for reduction of amino ketone derivatives such as P—N(Q)—CH(D)—CO—CH$_2$—X are well known to those of ordinary skill in the art (G. J. Quallich and T. M. Woodall, *Tetrahedron Lett.*, 34, p. 785 (1993) and references cited therein; and Larock, R. C. "Comprehensive Organic Transformations", pp. 527–547, VCH Publishers, Inc.© 1989 and references cited therein). A preferred reducing agent is sodium borohydride. The reduction reaction is typically conducted at a temperature of from about −40° C. to about 40° C. (preferably, at about 0° C. to about 20° C.), in a suitable solvent system such as, for example, aqueous or neat tetrahydrofuran or a lower alcohol, such as methanol or ethanol. Although this invention envisions both stereospecific and non-stereospecific reduction of the amino ketone derivative P—N(Q)—CH(D)—CO—CH$_2$—X, stereoselective reduction is preferred. Stereoselective reduction may be accomplished by use of chiral reagents known in the art or by the use of an achiral reducing agent on a chiral substrate. In the present invention, stereoselective reduction may be conveniently achieved, for instance, under non-chelating reducing conditions, where chiral induction of the newly formed hydroxyl group is set by the stereochemistry of the D group (i.e., Felkin-Ahn addition of hydride). We particularly prefer stereoselective reductions wherein the resulting hydroxyl is syn to D. We have found that when the hydroxyl group is syn to D, the final sulfonamide product is a more potent HIV protease inhibitor than its anti diastereomer.

The hydroxyl group of the amino alcohol may optionally be protected by any known oxygen protecting group (such as trialkylsilyl, benzyl, acetal or alkyloxymethyl) to yield a protected amino alcohol having the formula P—N(Q)—CH(D)—C(OR$^7$)—CH$_2$—X, wherein P, Q and D are as defined for compounds of formula II, X is a leaving group as defined above and R$^7$ is H or a suitable hydroxy protecting group. Several useful protecting groups are described in T. W. Greene and P. G. M. Wuts, *Protective Groups in Organic Synthesis*, 2d Ed., John Wiley and Sons (1991); L. Fieser and M. Fieser, *Fieser and Fieser's Reagents for Organic Synthesis*, John Wiley and Sons (1994); and L. Paquette, ed. *Encyclopedia of Reagents for Organic Synthesis*, John Wiley and Sons (1995).

The amino alcohol may then be reacted with a nucleophilic amine compound to form an intermediate of formula III:

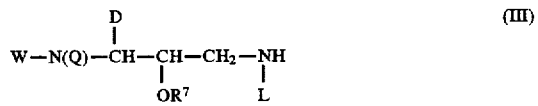

wherein W, Q and D are as defined in formula II, R$^7$ is H or any suitable oxygen protecting group and L is either D' (as described for compounds of formula I) or hydrogen.

Alternatively, an amino acid derivative may be reacted with a nucleophilic nitro compound (e.g., a nitromethane anion or a derivative thereof) which can be reduced in one or more steps to yield an intermediate of formula III.

In a particularly advantageous synthetic scheme, simultaneous activation of the methylene and protection of the alcohol may be accomplished by forming an N-protected amino epoxide from the oxygen and its adjacent methylene to give an intermediate of formula IV:

wherein W, Q and D are as defined above for compounds of formula II. Suitable solvent systems for preparing the N-protected amino epoxide include ethanol, methanol, isopropanol, tetrahydrofuran, dioxane, dimethylformamide and the like (including mixtures thereof). Suitable bases for producing the epoxide include alkali metal hydroxides, potassium t-butoxide, DBU and the like. A preferred base is potassium hydroxide.

Alternatively, the N-protected amino epoxide may be prepared by reacting an (alkylthio) or (phenylthio)acetic acid dianion with a cyclic N-carboxyanhydride of a protected α-amino acid (such as BOC-Phe-NCA, available from Propeptide). A preferred acetic acid dianion is (methylthio)acetic acid dianion. The resulting amino ketone may then be reduced (e.g., with sodium borohydride). The resulting amino alcohol is readily converted to the amino epoxide by quaternization (e.g., with methyl iodide) followed by ring closure (using, for example, sodium hydride).

Reaction of the N-protected amino epoxide (or other suitably activated intermediate) with an amine is carried out neat, i.e. in the absence of solvent, or in the presence of a polar solvent such as lower alkanols, water, dimethylformamide or dimethylsulfoxide. The reaction can be carried out conveniently between about −30° C. and 120° C., preferably between about −5° C. and 100° C. Alternatively, the reaction may be carried out in the presence of an activating agent, such as activated alumina in an inert solvent, preferably an ether, such as diethyl ether, tetrahydrofuran, dioxane, or tert-butyl methyl ether, conveniently from about room temperature to about 110° C., as described by Posner and Rogers, *J. Am Chem. Soc.*, 99, p. 8208 (1977). Other activating reagents include lower trialkyl-aluminum species, such as triethylaluminum, or dialkylaluminum halide species, such as diethylaluminum chloride (Overman and Flippin, *Tetrahedron Letters*, p. 195 (1981)). Reactions involving these species are conveniently carried out in inert solvents such as dichloromethane, 1,2-dichloroethane, toluene, or acetonitrile between about 0° C. and about 110° C. Further methods of displacing leaving groups, or opening epoxides with amines or their equivalents such as azides or trimethylsilyl cyanide (Gassman and Guggenheim, *J. Am. Chem. Soc.* 104, p. 5849 (1982)), are known and will be apparent to those of ordinary skill in the art.

Compounds of formulae II, III and IV, and functionality-protected derivatives thereof, are useful as intermediates for the preparation of compounds of formula I. In those cases where L represents D', compounds of formula III may be converted to compounds of formula I by reaction with sulfonyl-activated species to form sulfonamides, sulfonyl ureas, thiocarbamates and the like. Methods for preparing such sulfonyl-activated species are well within the ordinary skill of the art. Typically, sulfonyl halides are used to obtain sulfonamides. Many sulfonyl halides are commercially available; others may be easily obtained using conventional synthetic techniques (Gilbert, E. E. "Recent Developments in Preparative Sulfonation and Sulfation" Synthesis 1969:3 (1969) and references cited therein; Hoffman, R. V. "M-Trifluoromethylbenzenesulfonyl Chloride" Org. Synth. Coll. Vol. VII. John Wiley and Sons (1990); Hartman, G. D. et. al. "4-Substituted Thiophene-and Furan-2-sulfonamides as Topical Carbonic Anhydrase Inhibitors" *J. Med. Chem.*, 35, p. 3822 (1992) and references cited therein. Sulfonyl ureas are usually obtained by the reaction of an amine with sulfuryl chloride or a suitable equivalent such as sulfuryl-bis-imidazole or sulfuryl-bis-N-methyl imidazole. Thiocarbamates are typically obtained by the reaction of an alcohol with sulfuryl chloride or a suitable equivalent such as sulfuryl-bis-imidazole or sulfuryl-bis-N-methyl imidazole.

In the case of compounds of formula III wherein L is hydrogen, conversion of the resultant primary amine to a secondary amine may be carried out by known techniques. Such techniques include reaction with an alkyl halide or alkyl sulfonate, or by reductive alkylation with an aldehyde or carboxylic acid or activated derivative thereof using, for instance, catalytic hydrogenation or sodium cyanoborohydride (Borch et al., *J. Am. Chem. Soc.*, 93, p. 2897 (1971)). Alternatively, the primary amine may be acylated followed by reduction with borane or another suitable reducing reagent, for example, as described by Cushman et al., *J. Org. Chem.*, 56, p. 4161 (1991). This technique is especially useful in compounds of formula III where W represents a protecting group such as tert-butoxycarbonyl (Boc) or benzyloxycarbonyl (Cbz) and Q is H or where both W and Q are benzyl.

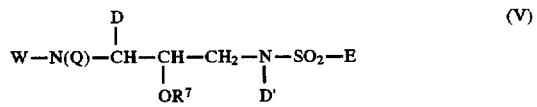
(V)

If variables W and Q of a particular compound of formula V represent removable protecting groups, removal of either or both groups followed by reaction of the resulting amine with an appropriate activated reagent will advantageously yield a different compound of formula V. For instance, reaction with an activated carboxylate, such as an acyl halide (e.g., acid fluorides, acid chlorides, and acid bromides), an activated ester such as 2- or 4-nitrophenyl esters, haloaryl esters (e.g., pentafluorophenyl or pentachlorophenyl) or 1-hydroxysuccinimide (HOSu) ester, a carbodiimide activated species, an anhydride, such as a symmetrical anhydride (e.g., isobutyl anhydride), or mixed carbonic-phosphoric or carbonic-phosphinic anhydrides, will yield the corresponding amide. Ureas may be obtained by reaction with isocyanates or amines in the presence of bis-activated carbonic acid derivatives such as phosgene or carbonyldiimdazole ("CDI"). Carbamates may be obtained by reaction with chlorocarbonates, with carbonates esterified with leaving groups such as 1-hydroxybenzotriazole ("HOBT"), HOSu, or 4-nitrophenol or with alcohols in the presence of bis-activated carbonic acid derivatives such as phosgene or its synthetic equivalents including diphosgene and triphosgene, or carbonyldiimdazole. An example of such a carbonate is N-succinimidyl-(3S)-tetrahydrofuran-3-yl carbonate. It will be readily recognized that in order to facilitate specific reactions, the protection of one or more potentially reactive groups followed by subsequent removal of that group may be required. Such modification to the reaction schemes outlined above are within the ordinary skill of the art.

A particularly useful synthetic scheme for producing preferred sulfonamide intermediates of formula VIII is shown below wherein for compounds of formulas VI, VII and VIII, W and Q are as defined above for compounds of formula II, D' and E are as defined for compounds of formula I, and P' is H or amino protecting groups:

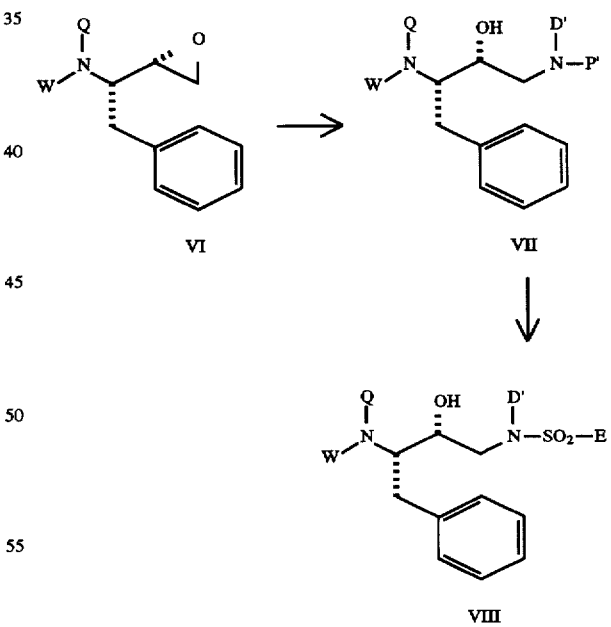

Compounds of formula VIII may be advantageously synthesized from readily available starting materials such as epoxide VI (see D. P. German, *J. Med. Chem.*, 36, p. 288 (1993) and B. E. Evans et al., *J. Org. Chem.*, 50, p. 4615 (1985)). Each step of the above synthetic scheme may be carried out as generally described above.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

The compounds of this invention may be modified by appending appropriate functionalites to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The novel compounds of the present invention are excellent ligands for aspartyl proteases, particularly HIV-1 and HIV-2 proteases. Accordingly, these compounds are capable of targeting and inhibiting late stage events in HIV replication, i.e., the processing of the viral polyproteins by HIV encoded proteases. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected cells. Compounds according to this invention advantageously inhibit the ability of the HIV-1 virus to infect immortalized human T cells over a period of days, as determined by an assay of extracellular p24 antigen—a specific marker of viral replication. Other antiviral assays have confirmed the potency of these compounds.

The compounds of this invention may be employed in a conventional manner for the treatment of viruses, such as HIV and HTLV, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally-infected patient in a pharmaceutically acceptable manner and in an amount effective to lessen the severity of the viral infection or to alleviate pathological effects associated with HIV infection or immunosuppression such as opportunistic infections or various cancers.

Alternatively, the compounds of this invention may be used in prophylactics and methods for protecting individuals against viral infection during a specific event, such as childbirth, or over an extended period of time. The compounds may be employed in such prophylactics either alone or together with other antiretroviral agents to enhance the efficacy of each agent. As such, the novel protease inhibitors of this invention can be administered as agents for treating or preventing HIV infection in a mammal.

The compounds of formula I, especially those having a molecular weight of less than about 700 g/mole, may be readily absorbed into the bloodstream of mammals upon oral administration. Compounds of formula I having a molecular weight of less than about 600 g/mole and aqueous solubility of greater than or equal to 0.1 mg/mL are most likely to demonstrate high and consistent oral availability. This surprisingly impressive oral availability makes such compounds excellent agents for orally-administered treatment and prevention regimens against HIV infection.

In addition to being orally bioavailable, the compounds of this invention also have an impressively high therapeutic index (which measures toxicity versus anti-viral effect). Accordingly, the compounds of this invention are effective at lower dosage levels than many previously described conventional antiretroviral agents and avoid many of the severe toxic effects associated with those drugs. The potential of these compounds to be delivered at doses far exceeding their effective antiviral levels is advantageous in slowing or preventing the possibility of resistant variants developing.

The compounds of this invention may be administered to a healthy or HIV-infected patient either as a single agent or in combination with other anti-viral agents which interfere with the replication cycle of HIV. By administering the compounds of this invention with other anti-viral agents which target different events in the viral life cycle, the therapeutic effect of these compounds is potentiated. For instance, the co-administered anti-viral agent can be one which targets early events in the life cycle of the virus, such as cell entry, reverse transcription and viral DNA integration into cellular DNA. Anti-HIV agents targeting such early life cycle events include, didanosine (ddI), dideoxycytidine (ddC), d4T, zidovudine (AZT), 3TC, 935U83, 1592U89, 524W91, polysulfated polysaccharides, sT4 (soluble CD4), ganiclovir, trisodium phosphonoformate, eflornithine, ribavirin, acyclovir, alpha interferon and trimetrexate. Additionally, non-nucleoside inhibitors of reverse transcriptase, such as TIBO, delavirdine (U90) or nevirapine, may be used to potentiate the effect of the compounds of this invention, as may viral uncoating inhibitors, inhibitors of trans-activating proteins such as tat or rev, or inhibitors of the viral integrase.

Combination therapies according to this invention exert an additive or synergistic effect in inhibiting HIV replication because each component agent of the combination acts on a different site of HIV replication. The use of such combination therapies may also advantageously reduce the dosage of a given conventional anti-retroviral agent which would be required for a desired therapeutic or prophylactic effect, as compared to when that agent is administered as a monotherapy. Such combinations may reduce or eliminate the side effects of conventional single anti-retroviral agent therapies, while not interfering with the anti-retroviral activity of those agents. These combinations reduce potential of resistance to single agent therapies, while minimizing any associated toxicity. These combinations may also increase the efficacy of the conventional agent without increasing the associated toxicity. In particular, we have discovered that in combination with other anti-HIV agents, the compounds of this invention act in an additive or synergistical manner in preventing the replication of HIV in human T cells. Preferred combination therapies include the administration of a compound of this invention with AZT, ddI, ddC, d4T, 3TC, 935U83, 1592U89, 524W91 or a combination thereof.

Alternatively, the compounds of this invention may also be co-administered with other protease inhibitors such as saquinavir (Ro 31-8959, Roche), MK 639 (Merck), ABT 538 (A-80538, Abbott), AG 1343 (Agouron), XM 412 (DuPont Merck), XM 450 (DuPont Merck), BMS 186318 (Bristol-Meyers Squibb) and CPG 53,437 (Ciba Geigy) or prodrugs of these or related compounds to increase the effect of therapy or prophylaxis against various viral mutants or members of HIV quasi species.

We prefer administering the compounds of this invention as single agents or in combination with retroviral reverse transcriptase inhibitors, such as nucleoside derivatives, or other HIV aspartyl protease inhibitors, including multiple combinations comprising from 3–5 agents. We believe that the co-administration of the compounds of this invention with retroviral reverse transcriptase inhibitors or HIV aspartyl protease inhibitors may exert a substantial additive or synergistic effect, thereby preventing, substantially reducing, or completely eliminating viral replication or infection or both, and symptoms associated therewith. Additionally, as the viruses are capable of developing resistance to certain aspartyl protease inhibitors quite rapidly, we believe that administration of a combination of agents may aid in slowing the development of resistant viruses relative to single agents alone.

The compounds of this invention can also be administered in combination with immunomodulators and immunostimulators (e.g., bropirimine, anti-human alpha interferon antibody, IL-2, GM-CSF, interferon alpha, diethyldithiocarbamate, tumor necrosis factor, naltrexone, tuscarasol, and rEPO); and antibiotics (e.g., pentamidine isethiorate) to prevent or combat infection and disease associated with HIV infections, such as AIDS, ARC and HIV-associated cancers.

When the compounds of this invention are administered in combination therapies with other agents, they may be administered sequentially or concurrently to the patient. Alternatively, pharmaceutical compositions according to this invention may comprise a combination of an aspartyl protease inhibitor of this invention and one or more therapeutic or prophylactic agents.

Although this invention focuses on the use of the compounds disclosed herein for preventing and treating HIV infection, the compounds of this invention can also be used as inhibitory agents for other viruses which depend on similar aspartyl proteases for obligatory events in their life cycle. These viruses include other AIDS-like diseases caused by retroviruses, such as simian immunodeficiency viruses, HTLV-I and HTLV-II. In addition, the compounds of this invention may also be used to inhibit other aspartyl proteases, and in particular, other human aspartyl proteases, including renin and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as dα-tocopherol polyethyleneglycol 1000 succinate, or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solublized derivatives may also be advantageously used to enhance delivery of compounds of formula I.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide or may be derivatized to bind to a stable resin as a tethered substrate for affinity chromatography applications. For example, a compound of formula I may be tethered to an affinity column to purify recombinantly produced HIV protease. Derivatization of the compounds of this invention to produce affinity chromatography resins and the methods used to purify proteases using such resins are well known and within the skill of the art. These and other uses which characterize commercial aspartyl protease inhibitors will be evident to those of ordinary skill in the art. (See: Rittenhouse, J. et al. *Biochem. Biophys. Res. Commun.* 171, p. 60 (1990) and Heimbach, J. C. et al. *Ibid* 164, p. 955 (1989)).

In order that this invention be more fully understood, the following examples are set forth. These examples are for the purpose of illustration only and are not to be construed as limiting the scope of the invention in any way.

General Materials and Methods

All temperatures are recorded in degrees Celsius. Thin layer chromatography (TLC) was carried out using 0.25 mm thick E. Merck silica gel 60 $F_{254}$ plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Thick layer silica gel chromatography was also carried out using E. Merck 60 $F_{254}$ plates ("prep plates") of 0.5, 1.0, or 2.0 mm thickness. Following development of the plate, the band of silica containing the desired compound was isolated and eluted with an appropriate solvent. Analytical HPLC was carried out using a Water's Delta Pak, 5 µM silica, C18 reversed-phase column, 3.9 mm ID×15 cm L with a flow rate of 1.5 mL/min using the following table:

Mobile phase:
A=0.1% $CF_3CO_2H$ in $H_2O$
B=0.1% $CF_3CO_2H$ in $CH_3CN$
Gradient:
T=0 min., A (95%), B (5%)
T=20 min., A (0%), B (100%)
T=22.5 min., A (0%), B (100%)

Preparative HPLC was also carried out using $C_{18}$ reversed-phase media. HPLC retention times were recorded in minutes. NMR spectral data was recorded using a Bruker AMX500, equipped with either a reverse or QNP probe, at 500 MHz, and was taken in the indicated solvent.

We have measured the inhibition constants of each compound against HIV-1 protease using the method described essentially by M. W. Pennington et al., *Peptides* 1990, Gimet, E. and D. Andrew, Eds., Escom; Leiden, Netherlands (1990).

Compounds of formula I were tested for their antiviral potency in several virological assays. In the first assay, the compounds were added as a solution in dimethylsulfoxide (DMSO) to a test cell culture of CCRM-CEM cells, a strain of $CD4^+$ human T-cell lymphoma cells, previously acutely infected with $HIV_{IIIb}$ using standard protocols (see Meek, T. D. et al., "Inhibition of HIV-1 protease in infected T-lymphocytes by synthetic peptide analogues", *Nature*, 343, p. 90 (1990). Preferred compounds are those which are able to inhibit 90% of viral infectivity at a concentration of 1 µM or less. More preferred compounds are those which are able to inhibit 90% of viral infectivity at a concentration of 100 nM or less.

The effect of the compounds on inhibiting the replication of the virus was measured by determining the HIV extracellular p24 antigen concentration using a commercial enzyme immunoassay (obtained from Coulter Corporation, Hialeah, Fla.).

Depending on the cell type and the desired readout, syncytia formation, reverse-transcriptase (RT) activity, or cytopathic effect as assayed by a dye uptake method may also be used as readouts of antiviral activity. See H. Mitsuya and S. Broder, "Inhibition of the in vitro infectivity and cytopathic effect of human T-lymphotropic virus type III/ lymphoadenopathy-associated virus (HTLV-III/LAV) by 2',3'-dideoxynucleosides", *Proc. Natl. Acad. Sci. USA*, vol.

83, pp. 1911–1915 (1986). The effect of compounds of formula I on clinical isolates of other HIV-1 strains was determined by obtaining low-passaged virus from HIV-infected patients and assaying the effect of the inhibitors in preventing infection of the HIV virus in freshly prepared human peripheral blood mononuclear cells (PBMCs).

Insofar as compounds of formula I are able to inhibit the replication of the HIV virus in human T-cells and furthermore, may be delivered orally to mammals, they are of evident clinical utility for the treatment of HIV infection. These tests are predictive of the compounds ability to inhibit HIV protease in vivo.

EXAMPLE 1

Synthesis of Compound 35

A. Compound VII (D'=isobutyl, W=tert-butoxy carbonyl, Q=H, P'=H). A solution of 4.1 g of epoxide VI (W=Boc, Q=H) in 30 mL of ethanol was treated with 22.4 mL of isobutylamine and heated under reflux for 1 h. The mixture was concentrated to yield the title compound as a white solid which was used without subsequent purification. NMR ($CDCl_3$): δ0.91 (d, 3H); 0.93 (d, 3H); 1.37 (s, 9H); 1.68 (br s, 2H); 2.40 (d, 2H); 2.68 (d, 2H); 2.87 (dd, 1H); 2.99 (dd, 1H); 3.46 (dd, 1H); 3.75 (br s, 1H); 3.80 (br s, 1H); 4.69 (d, 1H); 7.19–7.32 (m, 4H).

B. Compound 32. A solution of 391 mg of the resultant compound of Example 1A in 4:1 $CH_2Cl_2$/saturated aqueous $NaHCO_3$ was treated sequentially, at ambient temperature under an atmosphere of nitrogen, with 271 mg of 4-fluorobenzenesulfonyl chloride and 117 mg of sodium bicarbonate. The mixture was stirred for 14 h, diluted with $CH_2Cl_2$, washed with saturated NaCl then dried over $MgSO_4$, filtered, and concentrated in vacuo. The residue was purified by low pressure silica gel chromatography using 5% diethyl ether in $CH_2Cl_2$ as eluent to yield 420 mg of the title compound as a white solid. TLC: Rf=0.20, 5% diethyl ether in $CH_2Cl_2$. HPLC: Rt=17.41 min; ($^1$H)-NMR ($CDCl_3$) consistent with structure.

C. Compound VIII (W=H, Q=H, D'=isobutyl, E=4-fluorophenyl, hydrochloride salt). A solution of 398 mg of the resultant compound of Example 1B in ethyl acetate was treated at −20° C. with HCl gas. The HCl was bubbled through the mixture for 20 min over which time the temperature was allowed to warm to 20° C. Nitrogen was then bubbled through the mixture for 15 min and solvent removed in vacuo to yield 347 mg of the title compound as a white solid. TLC: Rf=0.82, 5:10:85 $NH_4OH/CH_3OH/CH_2Cl_2$; ($^1$H)-NMR ($CDCl_3$) consistent with structure.

D. Compound 35. A solution of 111 mg of the resultant compound of Example 1C in $CH_2Cl_2$ was added, at ambient temperature under an atmosphere of nitrogen, to a solution of 118 mg of N-succinimidyl-(S)-3-tetrahydrofuranyl carbonate (hereinafter "THF-OSu") and 133 mg N,N-diisopropylethylamine in $CH_2Cl_2$. The mixture was stirred for 14 h, diluted with $CH_2Cl_2$, washed with saturated $NaHCO_3$ and saturated NaCl, then dried over $MgSO_4$, filtered, and concentrated in vacuo. The residue was subjected to preparative thin layer silica gel chromatography using 5% $CH_3OH$ in $CH_2Cl_2$ to yield 98.8 mg of the title compound as a white solid. TLC: Rf=0.48, 5% $CH_3OH$ in $CH_2Cl_2$. HPLC: Rt=15.18 min; ($^1$H)-NMR ($CDCl_3$) consistent with structure.

EXAMPLE 2

Synthesis of Compound 101

A. Compound VII (W=tert-butoxycarbonyl, Q=H, D'=methyl, P'=H). To a solution of compound VI (W=Boc, Q=H) (1.7 mmol) in ethanol (20 mL) was added methylamine gas, at ambient temperature, for 30 min. The solution was stirred overnight, then concentrated under reduced pressure to give 0.47 g of the title compound which was used without subsequent purification. TLC: Rf=0.19, 1:10:90 $NH_4OH$/methanol/$CH_2Cl_2$. ($^1$H)-NMR ($CDCl_3$) consistent with structure.

B. Compound 128. To a solution of the product of Example 2A (0.15 g, 0.51 mmol) in $CH_2Cl_2$ (6 mL) was added a saturated solution of sodium bicarbonate (3 mL), followed by addition of solid sodium bicarbonate (90 mg, 1.0 mmol), followed by addition of acetamidobenzenesulfonyl chloride (0.24 g, 1.02 mmol). The mixture was stirred at ambient temperature overnight. The organics were extracted into 100 mL $CH_2Cl_2$, dried over anhydrous, $MgSO_4$, concentrated under reduced pressure then purified via medium pressure silica gel chromatography using a gradient system of $CH_2Cl_2$ followed by 5:95 EtOAc/$CH_2Cl_2$, followed by 10:90 EtOAc/$CH_2Cl_2$. The title compound was obtained as 244 mg of white solid. TLC: Rf=0.13, 3:97 methanol/$CH_2Cl_2$. HPLC: Rt=13.47 min; ($^1$H)-NMR ($CDCl_3$) consistent with structure.

C. Compound 101. This compound was prepared from the resultant compound of Example 2B by treatment with hydrogen chloride gas as described in Example 1C and subsequent reaction of this material with THF-OSu in the manner described in Example 1D. After workup and purification by preparative reversed-phase $C_{18}$ HPLC using a linear gradient of 35% to 100% $CH_3CN/H_2O$ with 0.1% TFA as eluant on a portion of the crude mixture, 4.2 mg of the title compound was obtained as a white solid. TLC: Rf=0.2, 4% MeOH/$CH_2Cl_2$. HPLC: Rt=11.53 min; ($^1$H)-NMR ($CDCl_3$) consistent with structure.

EXAMPLE 3

Synthesis of Compound 116

A. Aminomethylcyclopentane. To a solution of $LiAlH_4$ (38 g, 1.0 mole) in diethyl ether (2 L) was added cyclopentanecarbonitrile (73.2 g, 0.77 mol) as a solution in 250 mL ether. The solution was stirred overnight at ambient temperature and then quenched by addition of the organics to 3 L of a saturated potassium, sodium tartrate solution. The amine was extracted into 3 L of ether, dried over anhydrous $K_2CO_3$ then concentrated by distillation to approximately 400 mL total volume. The crude product was purified via distillation to give 58.2 g of the title compound as a colorless oil. ($^1$H)-NMR ($CDCl_3$) consistent with structure.

B. Compound VII (W=tert-butoxycarbonyl, Q=H, D'=cyclopentylmethyl, P'=H). To the resultant compound of Example 3A (20 g, 0.2 mol) was added compound VI (W=BOC, Q=H) (5.84 g) and the mixture was stirred for 24 h at ambient temperature. The solution was concentrated by distillation under reduced pressure. The residue was triturated with hexane and the solid collected by suction filtration and washed with hexane to give 7.08 g of a white solid which was used without further purification. TLC: Rf=0.59 (1:10:90 concentrated $NH_4OH$/methanol/$CDCl_2$). ($^1$H)-NMR ($CDCl_3$) consistent with structure.

C. Compound VIII (W=tert-butoxycarbonyl, Q=H, D'=cyclopentylmethyl, E=4-chlorophenyl). The resultant compound of Example 3B (252 mg) was reacted with 4-chlorobenzenesulfonyl chloride (175 mg) in the manner described in Example 8H. Workup and purification by silica gel chromatography using EtOAc/$CH_2Cl_2$ as eluant yielded the product as a white solid; ($^1$H) NMR ($CDCl_3$) consistent with structure.

D. Compound VIII (W=H, Q=H, D'=cyclopentylmethyl, E=4-chlorophenyl, hydrochloride salt). A solution of 320 mg of the resultant compound of Example 3C in 20 mL of EtOAc was treated with anhydrous HCl gas for 5 min. The reaction mixture was purged with nitrogen then concentrated in vacuo to yeld a white solid which was used directly for subsequent reaction.

E. Compound 116. To a solution of 63.4 $m_g$ of the resultant compound of Example 3D in 1 mL of THF was added sequentially 54 µL of diisopropylethylamine and a solution of 39.9 mg of THF-OSu in 1 mL THF. The mixture was stirred for 24 hours and then concentrated in vacuo. The residue was purified by low pressure silica gel column chromatography using 20% EtOAc in $CH_2Cl_2$ eluent to yield 0.62 g of the title compound. TLC: Rf=0.71, 40% EtOAc/$CH_2Cl_2$. HPLC: Rt=16.88 min. ($^1$H) NMR ($CDCl_3$) consistent with structure.

EXAMPLE 4

Synthesis of Compound 132

A. Compound VII (W=tert-butoxycarbonyl, Q=H, D'=(2-tetrahydrofuryl)-methyl, P'=H). To a solution of compound VI (W=Boc, Q=H) (3.3 mmol) in ethanol (30 mL) was added tetrahydrofurfurylamine (1.03 mL, 10 mmol). The mixture was warmed to 85° C. and stirred overnight. The solution was filtered and the solution concentrated under reduced pressure to give 1.29 g of the title compound which was used without subsequent purification. TLC: Rf=0.52, 1:10:90 $NH_4OH$/methanol/$CH_2Cl_2$ B. Compound 129. To a solution of the resultant compound of Example 4A (200 mg, 0.55 mmol) in $CH_2Cl_2$ (6 mL) was added 4-fluorobenzenesulfonyl chloride (320 mg, 1.6 mmol) followed a saturated solution of sodium bicarbonate (3 mL) and solid sodium bicarbonate (0.1 g, 1.2 mmol). The mixture was stirred at ambient temperature overnight. The solution was diluted with 100 mL $CH_2Cl_2$, the organics separated, dried over anhydrous $MgSO_4$, and the organics concentrated under reduced pressure. The crude product was purified via medium pressure liquid chromatography using a gradient solvent system of $CH_2Cl_2$ followed by 5:95 ether/$CH_2Cl_2$ followed by a 10:90 ether/$CH_2Cl_2$ solution to give 130 mg of the title compound as a white solid. TLC: Rf=0.35, 3:97 methanol/$CH_2Cl_2$. HPLC: Rt=16.37 min, ($^1$H)-NMR ($CDCl_3$) consistent with structure.

C. Compound VIII (W=E, Q=H, D'=(2-tetrahydrofuryl)-methyl, E=4-fluorophenyl, hydrochloride salt). To a solution of the resultant compound of Example 4B (30 mg, 0.057 mmol) in EtOAc (3 mL) was added 30% w/w HCl in EtOAc (1 mL). The mixture was stirred overnight at ambient temperature. The solution was concentrated under reduced pressure to give 16 mg of the title compound as a white solid which was used without subsequent purification. TLC: Rf=0.60 (1:10:90 $NH_4OH$/methanol/$CH_2Cl_2$).

D. Compound 132. To a solution of the resultant compound of Example 4C (16 mg) in $CH_2Cl_2$ (5 mL) was added triethylamine (0.1 mL, 0.72 mmol) followed by THF-OSu (20 mg, 0.09 mmol). The mixture was stirred at ambient temperature for 24 hours. The solution was concentrated under reduced pressure and the crude product purified via medium pressure column chromatography using 20:80 EtOAc/$CH_2Cl_2$ as the solvent system to give 7.4 mg. Rf=0.37 (3:97 methanol/$CH_2Cl_2$), HPLC: Rt=14.19 min, ($^1$H)-NMR ($CDCl_3$) consistent with structure.

EXAMPLE 5

Synthesis of Compound 134

A. Compound VII (W=tert-butoxycarbonyl, Q=H, D'=(isobutenyl, P'=H)). To a solution compound VI (W=tert-butoxycarbonyl, Q=H) (2.5 mmol) in ethanol (30 mL) was added a solution 2-methallylamine hydrochloride (1.34 g, 12.5 mmol) and KOH (0.70 g, 12.5 mmol) in ethanol (20 mL). The mixture stirred 30 min at ambient temperature. The solutions were combined and heated to 85° C. for 24 h. The solution was filtered and concentrated under reduced pressure to give 0.82 g of the title compound which was used without subsequent purification. TLC: Rf=0.45, 1:10:90 concentrated $NH_4OH$/methanol/$CH_2Cl_2$.

B. Compound 131. To a solution of the resultant compound of Example 5A (200 mg, 0.60 mmol) in $CH_2Cl_2$ (6 mL) was added 4-acetamidobenzenesulfonyl chloride (410 mg, 1.76 mmol), followed by a saturated solution of sodium bicarbonate (3 mL) and solid sodium bicarbonate (0.1 g, 1.2 mmol). The mixture was stirred at ambient temperature overnight. The solution was diluted with 100 mL $CH_2Cl_2$, the organics separated, dried over anhydrous $MgSO_4$, and the organics concentrated under reduced pressure. The crude product was purified via medium pressure liquid chromatography using a gradient solvent system of $CH_2Cl_2$, followed by 30:70 EtOAc/$CH_2Cl_2$ solution to give 140 mg of the title compound as a white solid. TLC: Rf=0.19, 3:97 methanol/$CH_2Cl_2$. HPLC: Rt=15.06 min, ($^1$H)-NMR ($CDCl_3$) consistent with structure.

C. Compound VIII (W=H, Q=H, D'=isobutenyl, E=4-acetamidophenyl, hydrochloride salt). To a solution of the resultant compound of Example 5B (40 mg 0.075 mmol) in EtOAc (5 mL) was added 30% w/w HCl in EtOAc (2 mL). The mixture was stirred overnight at ambient temperature. The solution was concentrated under reduced pressure to give the title compound, which was used without subsequent purification. TLC: Rf=0.38, 1:10:90 $NH_4OH$/methanol/$CH_2Cl_2$.

D. Compound 134. To a solution of the resultant compound of Example 5C in $CH_2Cl_2$ (5 mL) was added triethylamine (0.1 mL, 0.72 mmol), followed by THF-OSu (26 mg, 0.11 mmol). The mixture was stirred at ambient temperature for 24 hours. The solution was concentrated under reduced pressure and the crude product purified via medium pressure column chromatography using a gradient solvent system of $CH_2Cl_2$, followed by 1:99 methanol/$CH_2Cl_2$, followed by 3:97 methanol/$CH_2Cl_2$ as the solvent system to give 10.1 mg of the title compound. Rf=0.11 (3:97 methanol/$CH_2Cl_2$), HPLC: Rt=12.86 min, ($^1$H)-NMR ($CDCl_3$) consistent with structure.

EXAMPLE 6

Synthesis of Compound 136

A. Compound VII (W=tert-butoxycarbonyl, Q=H, D'=2-furfuryl, P'=H). To a solution compound VI (W=Boc, Q=H) (2.5 mmol) in ethanol (30 mL) was added furfurylamine (0.67 mL, 7.5 mmol) and the mixture was heated to 85° C. for 24 h. The solution was filtered and concentrated under reduced pressure to give 0.80 g of the title compound which was used without subsequent purification. TLC: Rf=0.38, 1:10:90 concentrated $NH_4OH$/methanol/$CH_2Cl_2$.

B. Compound VIII (W=tert-butoxycarbonyl, Q=H, D'=2-furyl, E=4-fluorophenyl). To a solution of the product of Example 6A (0.20 g, 0.60 mmol) in $CH_2Cl_2$ (6 mL) was added a saturated solution of sodium bicarbonate (3 mL), followed by addition of solid sodium bicarbonate (0.1 g, 1.2 mmol), then p-fluorobenzenesulfonyl chloride (0.32 g, 1.6 mmol). The mixture was stirred at ambient temperature for 24 h. The organics were extracted into 100 mL $CH_2Cl_2$, dried over anhydrous $MgSO_4$, concentrated under reduced pressure, then purified via medium pressure silica gel chromatography using a gradient system of $CH_2Cl_2$, followed by 1:99 methanol/$CH_2Cl_2$. The title compound was obtained as a white solid (86.1 mg). TLC: Rf=0.17, 3:97 methanol/$CH_2Cl_2$. HPLC: Rt=16.5 min; ($_1$H)-NMR ($CDCl_3$) consistent with structure.

C. Compound VIII (W=H, Q=H, D'=2-furyl, E=4-fluorophenyl, hydrochloride salt). To a solution of the resultant compound of Example 6B (16 mg, 0.031 mmol) in EtOAc (3 mL) was added 30% w/w HCl in EtOAc (1 mL). The mixture was stirred overnight at ambient temperature. The solution was concentrated under reduced pressure to give the title compound, which was used without subsequent purification. TLC: Rf=0.48, 1:10:90 $NH_4OH$/methanol/$CH_2Cl_2$.

D. Compound 136. To a solution of the resultant compound of Example 6C in $CH_2Cl_2$ (5 mL) was added triethylamine (0.1 mL, 0.72 mmol), followed by THF-OSu (11 mg, 0.05 mmol). The mixture was stirred at ambient temperature for 24 hours. The solution was concentrated under reduced pressure and the crude product purified via medium pressure column chromatography using a gradient solvent system of $CH_2Cl_2$ followed by 20:80 EtOAc/$CH_2Cl_2$ as the solvent system to give 4.9 mg. TLC: Rf=0.28, (3:97 methanol/$CH_2Cl_2$, HPLC: Rt=14.57 min, ($_1$H)-NMR ($CDCl_3$) consistent with structure.

EXAMPLE 7

Synthesis of Compound 158

A. Compound VII (W=tert-butoxycarbonyl, Q=H, D'=cyclohexylmethyl, P'=H). To a solution of compound VI (W=Boc, Q=H) (5.0 mmol) in ethanol (20 mL) was added cyclohexylmethylamine (3.25 mL, 2.83 mmol) and the mixture was stirred for 3 hours at ambient temperature. The solution was filtered and concentrated under reduced pressure to give 1.49 g of a white solid which was used directly for subsequent reaction. TLC: Rf=0.14, 3:97 methanol/$CH_2Cl_2$. ($^1$H)-NMR ($CDCl_3$) consistent with structure.

B. Compound VIII (W=tert-butoxycarbonyl, Q=H, D'=cyclohexylmethyl, E=4-methoxyphenyl). To a solution of the resultant compound of Example 7A (400 mg, 1.06 mmol) in $CH_2Cl_2$ (10 mL) was added 4-methoxybenzenesulfonyl chloride (0.66 g, 3.1 mmol) followed by addition of a saturated solution of sodium bicarbonate (3 mL) and 0.18 g of solid sodium bicarbonate. The mixture was stirred at ambient temperature overnight. The solution was diluted with 200 mL $CH_2Cl_2$, the organics separated, dried over anhydrous $MgSO_4$, and the organics concentrated under reduced pressure. The crude product was purified via medium pressure liquid chromatography using $CH_2Cl_2$, followed by 1:99 methanol/$CH_2Cl_2$ as the solvent system to give 340 mg of the title compound as a white solid. TLC: Rf=0.39, 3:97 methanol/$CH_2Cl_2$, ($^1$H)-NMR (CDCL$_3$) consistent with structure.

C. Compound VIII (W=H, Q=H, D'=cyclohexylmethyl, E=4-methoxyphenyl, hydrochloride salt). To a solution of the resultant compound of Example 7B (0.34 g, 0.62 mmol) in EtOAc (10 mL) was added 30% w/w HCl in EtOAc (5 mL). The mixture was stirred for 3 hours at ambient temperature. The solution was concentrated under reduced pressure to give 0.3 g of a white solid which was used directly for subsequent reaction. TLC: Rf=0.12, 3:97 methanol/$CH_2Cl_2$.

D. Compound 158. To a solution of the resultant compound of Example 7C (100 mg, 0.21 mmol) in $CH_2Cl_2$ (8 mL) was added triethylamine (0.2 mL, 1.44 mmol) followed by THF-OSu (71 mg, 0.31 mmol). The mixture was stirred at ambient temperature for 6 hours. The solution was diluted with $CH_2Cl_2$, (200 mL) washed with a saturated solution of sodium bicarbonate (30 mL), the organics separated, dried over anhydrous $MgSO_4$ and concentrated under reduced pressure and the crude product purified via medium pressure column chromatography using a gradient solvent system of $CH_2Cl_2$ followed by 10:90 EtOAc/$CH_2Cl_2$ as the solvent system to give 84.9 mg of the title compound. TLC: Rf=0.48, 3:97 methanol/$CH_2Cl_2$, HPLC: Rt=16.35 min; ($^1$H)-NMR ($CDCl_3$) consistent with structure.

EXAMPLE 8

Synthesis of Compound 195

A. 3(S)-amino-2(syn)-hydroxy-4-phenyl-1-chlorobutane formate salt. To a slurry of 16.33 g of 10% palladium on carbon (25% by weight) in methanol and tetrahydrofuran (400 mL, 1:1) was added, under $N_2$, 65.35 g of 3(S)-N-(-benzyloxycarbonyl)-amino-1-chloro-2(syn)-hydroxy-4-phenylbutane (195.77 mmol) as a solution in methanol and tetrahydrofuran (1.2 L). To this slurry was added 540 mL of formic acid. After 15 h, the reaction mixture was filtered through diatomaceous earth and concentrated to dryness. The resultant oil was slurried in toluene and evaporated, then triturated sequentially with diethyl ether and $CH_2Cl_2$ to provide 47.64 g of product as a granular tan solid. TLC: Rf=0.17, 5% acetic acid/ethyl acetate.

B. 3(S)-N-(3(S)-tetrahydrofuryloxycarbonyl)-amino-1-chloro-2(syn)-hydroxy-4-phenylbutane. To a solution of the resultant compound of Example 8A (1.97 g, 7.95 mmol) in $CH_2Cl_2$ (20 mL) was added a saturated solution of sodium bicarbonate (5 mL), followed by solid sodium bicarbonate (1.33 g, 17.9 mmol), and THF-OSu (2.0 g, 8.7 mmol). The mixture was stirred at ambient temperature overnight. The solution was diluted with 200 mL $CH_2Cl_2$, the organics separated, dried over anhydrous $MgSO_4$, and concentrated under reduced pressure. The residue was recrystallized from ethyl acetate/hexane to give 1.01 g of the title compound as a white solid. TLC: Rf=0.35, 3:97 methanol/$CH_2Cl_2$. ($^1$H)-NMR ($CDCl_3$) consistent with structure.

C. Compound VI (W=H, Q=3(s)-tetrahydrofuryloxycarbonyl). To a solution of the resultant compound of Example 8B (1.0 g, 3.2 mmol) in absolute ethanol (15 mL) was added solid KOH (0.21 g, 3.8 mmol). The mixture was stirred at ambient temperature for 1.0 h. The solution was filtered through a pad of Celite then concentrated under reduced pressure. The residue was taken up in ether (100 mL), washed with brine, dried over $MgSO_4$, the concentrated under reduced pressure to give 0.88 g of the title compound as a white solid. TLC: Rf=0.49 (3:97 methanol/$CH_2Cl_2$), ($^1$H)-NMR ($CDCl_3$) consistent with structure.

D. Compound III (W=H, Q=(S)-3-tetrahydrofuryloxycarbonyl, D=benzyl, D'=cyclopentylmethyl, $R_7$=H, L=H). The resultant compound of Example 8C (0.88 g, 3.2 mol) was added to the resultant compound of Example 3A (5.0 g, 50.4 mmol) and stirred for 24 h at ambient temperature. The solution was concentrated by distillation under reduced pressure. The residue was triturated with hexane and the solid collected by suction filtration and washed with hexane to give 0.93 g of the title compound. TLC: Rf=0.44, 1:10:90 concentrated $NH_4OH$/methanol/$CH_2Cl_2$; ($^1$H)-NMR ($CDCl_3$) consistent with structure.

E. Compound VII (W=H, Q=(S)-3-tetrahydrofuryl, D'=cyclopentylmethyl, P'=tert-butoxycarbonyl). To a solution of 264 mg of the resultant compound of Example 8D in 10 mL of $CH_2Cl_2$ was added 0.14 mL of disopropylethylamine and 175 mg of di-tert butylpyrocarbonate. After stirring for 4 hours, the mixture was diluted with 50 mL of $CH_2Cl_2$, washed with 0.5N of HCl and brine, dried over magnesium sulfate, filtered and concentrated in vacuo to yield 364 mg of the title compound as a white solid which was used without subsequent purification. TLC: Rf=0.58, 40% EtOAc/$CH_2Cl_2$.

F. A solution of 334 mg of the resultant compound of Example 8E in 5 mL of ethanol was hydrogenated under 30 psi of hydrogen in the presence of 80 mg of platinum (IV) oxide for 24 hours. The mixture was filtered and concentrated. The residue was purified by a low pressure silica gel column chromatography using 20% EtOAc in $CH_2Cl_2$ eluent to yield 268 mg of the title compound. TLC: Rf=0.55, 40% EtOAc/$CH_2Cl_2$. ($^1$H)-NMR (CDCl$_3$) consistent with structure.

G. A solution of 268 mg of the resultant compound of Example 8F in 10 mL of EtOAc was treated with anhydrous HCl gas for 5 min. The reaction mixture was purged with nitrogen then concentrated in vacuo and the resulting white solid used without subsequent purification for subsequent reaction.

H. Compound 195. To a solution of 233 mg of the crude resultant compound of Example 8G in 10 mL of $CH_2Cl_2$ was added 2 mL of saturated aqueous sodium bicarbonate and 149 mg of 4-methyloxybenzene sulfonyl chloride. After 3 hours, the resulting mixture was diluted with $CH_2Cl_2$, washed with sodium bicarbonate, brine, dried over magnesium sulfate, filtered and concentrated in vacuo. The residue was purified by low pressure silica gel column chromatography using 0% to 20% EtOAc/$CH_2Cl_2$ to yield 225 mg of the title compound as a white solid. TLC: Rf=0.40, 20% EtOAc/$CH_2Cl_2$; HPLC: Rt=15.65 min.: ($^1$H)NMR (CDCl$_3$) consistent with structure.

EXAMPLE 9

Synthesis of Compound 196

A. (1S,2 syn)-N-(1-Isobutyl-3-chloro-2-hydroxypropyl) benzyloxycarbonylamine. To a solution of N-Cbz-leucine chloromethyl ketone (2.0 g) in 20 mL of methanol was added, at 0° C., 1.0 g of sodium borohydride and the mixture was stirred at ambient temperature for 24 h. The solution was concentrated under reduced pressure and the residue partitioned between 20 mL of saturated aqueous $NH_4Cl$ and 500 ml of diethyl ether. The organic fraction was separated, dried over $MgSO_4$ and concentrated in vacuo and the residue purified by silica gel chromatography to yield 1.8 g of white solid.

B. (1S, 2S)-N-(1-Isobutyl-2,3-epoxypropyl) benzyloxycarbonylamine. To a solution of the resultant compound of Example 9A (300 mg) in absolute ethanol was added 67 mg of powdered KOH. The mixture was stirred for 3 h at ambient temperature, filtered through diatomaceous earth, and concentrated in vacuo. The residue was dissolved in diethyl ether, dried over $MgSO_4$, and concentrated to yield 230 mg of colorless oil, which was used directly for subsequent reaction.

C. (2R,3S)-$N^3$-Carbobenzyloxy-$N^1$-isobutyl-1,3-diamino-2-hydroxy-5-methylhexane. A 230 mg portion of the resultant compound of Example 9B was suspended in 5 mL of isobutylamine and the mixture stirred overnight at ambient temperature. The mixture was concentrated in vacuo to yield the title product as 179 mg of a white solid, which was used directly for subsequent reaction.

D. Compound V (W=benzyloxycarbonyl, Q=H, D=isobutyl, D'=isobutyl, $R^7$=H, E=4-methoxyphenyl, (S)-hydroxy). Following the procedure described in Example 8H, a solution of the resultant compound of Example 9C (170 mg) in $CH_2Cl_2$ was reacted with 4-methoxybenzenesulfonyl chloride (150 mg) in the presence of aqueous $NaHCO_3$. Workup and silica gel chromatography yielded 90 mg of product as a white solid.

E. Compound V (W=H, Q=H, D=isobutyl, D'=isobutyl, $R^7$=H, E=4-methoxyphenyl, (syn)-hydroxy). A solution of the resultant compound of Example 9D (90 mg) in ethanol was treated with 50 mg of 10% palladium on carbon and the mixture stirred under an atmosphere of hydrogen. After completion of reaction, the mixture was filtered and concentrated in vacuo to yield 60 mg of the title compound which was used directly for subsequent reaction.

F. Compound 196. Reaction of the resultant compound of Example 9E (60 mg) in $CH_2Cl_2$ was reacted with THF-OSu (150 mg) as described earlier yielded, following aqueous workup, drying over $MgSO_4$, filtering, and concentration in vacuo, a residue which was purified by silica gel chromatography using methanol/$CH_2Cl_2$ as eluant to yield the title product as 40 mg of white solid. [$^1$H]-NMR(CDCl$_3$) consistent with structure.

EXAMPLE 10

Synthesis of Compound 203

A. The epoxide prepared in Example 9B (0.430 g, 1.63 mmol) and cyclopentylmethylamine (2.50 g, 25.0 mmol) were stirred at R.T. for 48 h. The solution was diluted with 25 mL of ethanol and concentrated under reduced pressure. The crude material was purified via MPLC (gradient: $CH_2Cl_2$; 1% MeOH/$CH_2Cl_2$; $CH_2Cl_2$/MeOH/$NH_4OH$, 95:5:1) to give 430 mg (73%) of the amine product. [$^1$H]-NMR(CDCl$_3$) consistent with structure.

B. The amine prepared in Example 10A (0.120 g, 0.331 mmol) was subjected to the procedure described in Example 7B. Purification of the crude material via MPLC (gradient: $CH_2Cl_2$; 2% $Et_2O$/$CH_2Cl_2$) gave 10 mg of Fraction A (2 syn, 3S isomer) and 70 mg of Fraction B (2R, 3S isomer). [$^1$H]-NMR (CDCl$_3$) consistent with structures.

C. The Cbz-amine Fraction A prepared in Example 10B (0.010 g, 0.019 mmol) was taken up in 5 mL of absolute ethanol and Pd/C (15 mg) was added. The mixture was stirred under an atmosphere of hydrogen for 24 h. The solution was filtered and concentrated under reduced pressure to give the amine product in quantitative yield. This material was used without further purification.

D. The amine prepared in Example 10C (0.010 g, 0.025 mmol) was used in the procedure described in Example 1D. Purification of the crude material via MPLC (gradient: $CH_2Cl_2$; 1% MeOH/$CH_2Cl_2$) gave 2.8 mg (29%) of compound 203.

EXAMPLE 11

Synthesis of Compound 212

A. A 1.12 portion of anhydrous DMF is cooled to 0° C. and treated dropwise with 2.06 g of sulfuryl chloride. The resulting suspension is stirred for 30 min., then treated with 1.50 g of benzyl phenyl ether. The mixture is heated at 90° C. for 3 h, then cooled, extracted with brine and methylene chloride, and dried over $MgSO_4$. Chormotography on silica gel (i-PrOH/hexanes) yields 4-benzyloxybenzenesulfonyl chloride.

B. The amine prepared in Example 7A (0.150 g, 0.398 mmol) and 4-(phenylmethoxy)benzenesulfonyl chloride (0.170 g, 0.601 mmol) were utilized in the procedure described in Example 7B to give after MPLC purification (gradient: $CH_2Cl_2$; 5% $Et_2O/CH_2Cl_2$; 10% $Et_2O/CH_2Cl_2$) 120 mg (48%) of Cbz-amine. [$^1$H]-NMR($CDCl_3$) consistent with structure.

C. The Cbz-amine prepared in Example 11B (0.120 g, 0.214 mmol) was subjected to the procedure described in Example 10C to give 50 mg (59%) of the crude amine which was used without further purification.

D. The amine prepared in Example 11C (0.050 g, 0.125 mmol) was used in the procedure described in Example 1D. Purification of the crude material via MPLC (gradient: $CH_2Cl_2$; 1% MeOH/$CH_2Cl_2$; 2% MeOH/$CH_2Cl_2$) gave compound 212. [$^1$H]-NMR($CDCl_3$) consistent with structure.

EXAMPLE 12

Synthesis of Compound 213

A. The epoxide described in Example 9B (0.53 g, 2.01 mmol) was reacted with 2-phenylethylamine (5.0 mL, 40 mmol) as described in Example 9C to give 640 mg (83% yield) of the amine after MPLC purification (gradient: $CH_2Cl_2$; 1% then 5% then 10% MeOH/$CH_2Cl_2$).

B. The amine prepared in Example 12A (0.150 g, 0.39 mmol) was subjected to the procedure described in Example 11B to give after MPLC purification (gradient: $CH_2Cl_2$; 5% then 10% methanol/$CH_2Cl_2$) 110 mg (45%) of the Cbz-amine. [$^1$H]-NMR($CDCl_3$) consistent with structure.

C. The Cbz-amine prepared in Example 12B (0.110 g, 0.177 mmol) was treated as described in Example 10C to give 40 mg (56%) of the amine which was used without further purification. [$^1$H]-NMR($CDCl_3$) consistent with structure.

D. The amine prepared in Example 12C (0.040 g, 0.098 mmol) was treated as described in Example 1D. Purification of the crude material via MPLC (gradient: $CH_2Cl_2$; 1% MeOH/$CH_2Cl_2$; 2% MeOH/$CH_2Cl_2$) gave compound 213. [$^1$H]-NMR($CDCl_3$) consistent with structure.

EXAMPLE 13

Synthesis of Compound 223

A. The procedure described in Example 1A was performed using 30 mg of epoxide VI (W=Boc, Q=H) and 2-pyrrolidinylethylamine (0.200 g, 1.75 mmol) to give 25 mg (58%) of Boc-amine after chromatography ($CHCl_3$/MeOE, 2:1). [$^1$H]-NMR($CDCl_3$) consistent with structure.

B. The procedure described in Example 7B was performed using the amine prepared in Example 13A (0.040 g, 0.106 mmol) and substituting potassium bicarbonate for sodium bicarbonate (in both solid and aqueous solution forms) to give 30 mg (52%) of BOC-amine sulfonamide after chromatography ($CHCl_3$/MeOH, 5:1). [$^1$H]-NMR($CDCl_3$) consistent with structure.

C. The BOC-amine sulfonamide prepared in Example 13B (0.008 g, 0.015 μmol) was dissolved in acetonitrile and treated with 2N HCl. The solvents were removed and the material dried over $MgSO_4$. This crude material was subjected to the procedure described in Example 1D to give 5 mg (59%) of compound 223 after chromatography ($CHCl_3$/MeOH, 10:1). [$^1$H]-NMR($CDCl_3$) consistent with structure.

EXAMPLE 14

Synthesis of Compound 224

A. Cyclopentylacetic acid (5.2 g, 41 mmol) and thionyl chloride (10 mL) were combined then DMF (0.2 mL) was added and the solution was stirred 1.5 h at R.T. Dichloromethane (10 mL) was added and the solution cooled in an ice bath whereupon 25% aqueous ammonia (30 mL) was added and the mixture stirred for 0.5 h. The solution was extracted with $CH_2Cl_2$ (3×) and the combined extracts washed with 1N HCl, dried over $MgSO_4$, and concentrated to give cyclopentylacetamide (2.699 g, 52%). [$^1$H]-NMR ($CDCl_3$) consistent with structure.

B. Cyclopentylacetamide (2.70 g, 21.0 mmol) was dissolved in 100 mL of $Et_2O$ whereupon lithium aluminum hydride (2.2 g, 58 mmol) was added and the mixture was heated to 60° C. for 4 h. Following standard work-up conditions the crude material was distilled to give 2-cyclopentylethylamine (750 mg, 32%); b.p.: 78° C. at 40 mm Hg. [$^1$H]-NMR ($CDCl_3$) consistent with structure.

C. The procedure described in Example 1A was performed using 14 mg of epoxide VI (W=Boc, Q=H) and 2-cyclopentylethylamine (0.045 g, 0.40 mmol) to give 12 mg (64%) of Boc-amine after chromatography ($CHCl_3$/MeOH/$NH_4OH$; 90:10:1). [$^1$H]-NMR($CDCl_3$) consistent with structure.

D. The BOC-amine prepared in Example 14C (0.188 g, 0.5 mmol) was dissolved in $CH_2Cl_2$ and TEA (0.09 mL) and 4-methoxybenzenesulfonyl chloride (0.124 g, 0.6 mmol) were added. After stirring for 2 h the mixture was washed with saturated aq. $NaHCO_3$ (3×), 10% aq. HCl (3×), and dried over $MgSO_4$ to give 240 mg (88%) of BOC-amine sulfonamide after chromatography (hexanes/EtOAc; 8:2). [$^1$H]-NMR($CDCl_3$) consistent with structure.

E. The BOC-amine sulfonamide prepared in Example 14D (0.235 g, 0.43 mmol) was taken up in EtOAc and treated with HCl to give 214 mg (quantitative) of crude amine-HCl salt which was used without further purification.

F. The crude amine-HCl salt prepared in Example 14E (0.211 g, 0.43 mmol) was treated as described in Example 1D to give 178 mg (74%) of compound 224. [$^1$H]-NMR ($CDCl_3$) consistent with structure.

EXAMPLE 15

Synthesis of Compound 225

A. 4-Piperidinecarboxamide (10.2 g, 78.0 mmol) in DMSO (10 mL) was treated with benzyl bromide (20.0 mL, 168 mmol). The mixture was diluted with EtOAc and washed with 1N aq. HCl, 5N aq. NaOH, dried over $MgSO_4$, and concentrated to give 5.90 g (35%) of N-benzyl-4-piperidinecarboxamide. [$^1$H]-NMR($CDCl_3$) consistent with structure.

B. The N-benzyl-4-piperidinecarboxamide (2.19 g, 10 mmol) was treated as described in Example 14B to give 2.01 g (98%) of the amine. [$^1$H]-NMR($CDCl_3$) consistent with structure.

C. The procedure described in Example 1A was performed using 100 mg of epoxide VI (W=Boc, Q=H) and the amine prepared in Example 15B (0.100 g, 0.78 mmol) to give 25 mg (14%) of Boc-amine after chromatography (hexanes:EtOAc; 10:1). [$^1$H]-NMR($CDCl_3$) consistent with structure.

D. The procedure described in Example 14D was performed using the BOC-amine prepared in Example 15C (0.106 g, 0.23 mmol) to give 92 mg (65%) of the sulfonamide. [$^1$H]-NMR($CDCl_3$) consistent with structure.

E. The sulfonamide prepared in Example 15D (0.065 g, 0.10 mmol) was treated as described in Example 14E to give 64 mg of crude amine-HCl salt. [$^1$H]-NMR($CDCl_3$) consistent with structure.

F. The crude amine-HCl salt prepared in Example 15E (0.055 g, 0.092 mmol) was treated as described in Example 1D to give 51 mg (85%) of N-benzylpiperidine. [$^1$H]-NMR (CDCl$_3$) consistent with structure.

G. The N-benzylpiperidine (0.055 g, 0.092 mmol), prepared in Example 15F was treated as described in Example 10C to give a crude product which upon purification by chromatography (CH$_2$Cl$_2$/MeOH/NH$_4$OH; 90:10:1) gave compound 225. [$^1$H]-NMR(CDCl$_3$) consistent with structure.

EXAMPLE 16

Synthesis of Compound 228

A. 4-Hydroxypiperidine (10.8 g, 107 mmol) and Et$_3$N (17 mL, 123 mmol) in 80 mL of CH$_2$Cl$_2$ was cooled in an ice bath whereupon benzyl chloroformate (16.3 mL, 114 mmol) was added. After stirring 1.5 h at R.T. the mixture was subjected to standard work-up conditions to give 13.9 g (55%) of N-Cbz-piperidine after chromatography (CHCl$_3$/MeOH; 10:1). [$^1$H]-NMR(CDCl$_3$) consistent with structure.

B. A solution of DEAD (1.61 mL, 10.2 mmol) in 20 mL of THF was added to a solution of triphenylphosphine (2.69 g, 10.3 mmol), the N-Cbz-piperidine prepared in Example 16A (2.36 g, 100 mmol) and phthalimide (1.50 g, 10.2 mmol) in 80 mL of THF. After stirring 10.5 h at R.T. the mixture was quenched with water, extracted with EtOAc (3×) and the combined extracts washed with brine solution, dried over Na$_2$SO$_4$ and concentrated to give the crude product. Purification of this material by chromatography (hexanes/EtOAc; 2:1) gave 1.81 g, (50%) of 1-benzyloxycarbonyl-4-phthalimidylpiperidine. [$^1$H]-NMR(CDCl$_3$) consistent with structure.

C. 1-Benzyloxycarbonyl-4-phthalimidylpiperidine (1.50 g, 4.27 mmol), prepared in Example 16B, was taken up in 20 mL of ethanol. To this solution was added hydrazine monohydrate (35 mL, 700 mmol) and this mixture was heated at 100° C. for 3 h. Brine solution (40 mL) and 10% aq. K$_2$CO$_3$ (60 mL) were added and the mixture was extracted with 5% MeOH/CHCl$_3$ (3×). The combined extracts were washed with 2N aq. HCl, 2N aq. NaOH, brine solution, dried over Na$_2$SO$_4$ and concentrated to give 0.847 g, (85%) of 4-amino-1-benzyloxycarbonylpiperidine. [$^1$H]-NMR (CDCl$_3$) consistent with structure.

D. The procedure described in Example 1A was performed using 132 mg of epoxide VI (W=Boc, Q=H) and 4-amino-1-benzyloxycarbonylpiperidine (0.353 g, 1.51 mmol), prepared in Example 16C, to give 168 mg (67%) of Boc-amine after chromatography (CHCl$_3$/MeOH/NH$_4$OH; 95:5:1). [$^1$H]-NMR(CDCl$_3$) consistent with structure.

E. The procedure described in Example 14D was performed using the BOC-amine prepared in Example 16D (0.059 g, 0.320 mmol) to give the crude product which after chromatography (CHCl$_3$/MeOH/NH$_4$OH; 95:5:1) gave 141 mg (66%) of the sulfonamide. [$^1$H]-NMR(CDCl$_3$) consistent with structure.

F. The sulfonamide prepared in Example 16E (0.050 g, 1.57 mmol) was treated as described in Example 14E to give 971 mg of crude amine-HCl salt. [$^1$H]-NMR(CDCl$_3$) consistent with structure.

G. The crude amine-HCl salt prepared in Example 16F (0.118 g, 0.207 mmol) was treated as described in Example 1D to give 147 mg of crude carbamate. [$^1$H]-NMR(CDCl$_3$) consistent with structure.

H. The crude carbamate prepared in Example 16G (0.116 g, 0.163 mmol) was treated as described in Example 10C. Purification of the crude material by chromatography (CHCl$_3$/MeOH/NH$_4$OH; 95:5:1) gave 28 mg (31%) of the compound 228. [$^1$H]-NMR(CDCl$_3$) consistent with structure.

EXAMPLE 17

Synthesis of Compound 233

A. The procedure described in Example 1A was performed using epoxide VI (W=Boc, Q=H) (0.030 g, 0.11 mmol) and 2,2-dimethyl-3-hydroxypropylamine (0.24 g, 0.23 mmol) to give 42 mg (quantitative) of Boc-amine after chromatography (CHCl$_3$/MeOH/NH$_4$OH; 100:10:1). [$^1$H]-NMR(CDCl$_3$) consistent with structure.

B. The procedure described in Example 14D was performed using the BOC-amine prepared in Example 17A (0.030 g, 0.082 mmol) to give the crude product which after chromatography (CHCl$_3$/MeOH/NH$_4$OH; 150:10:1) gave 42.8 mg (95%) of the sulfonamide. [$^1$H]-NMR(CDCl$_3$) consistent with structure.

C. The sulfonamide prepared in Example 17B (0.030 g, 0.056 mmol) was treated as described in Example 14E to give 29.3 mg of crude amine-HCl salt. [$^1$H]-NMR(CDCl$_3$) consistent with structure.

D. The crude amine-HCl salt prepared in Example 17C (0.029 g, 0.061 mmol) was treated as described in Example 1D to give 21.1 mg (69%) of compound 233. [$^1$H]-NMR (CDCl$_3$) consistent with structure.

EXAMPLE 18

Synthesis of Compound 234

A. The procedure described in Example 1A was performed using epoxide VI (W=Boc, Q=H) (0.200 g, 0.76 mmol) and 2-aminothiazole (1.2 g, 12.0 mmol) to give 150 mg (54%) of Boc-amine after chromatography (CHCl$_3$/MeOH; 10:1). [$^1$H]-NMR(CDCl$_3$) consistent with structure.

B. The procedure described in Example 14D was performed using the BOC-amine prepared in Example 18A (0.004 g, 0.011 mmol) to give the crude product which after chromatography (CHCl$_3$/EtOAc; 3:4) gave the sulfonamide. [$^1$H]-NMR(CDCl$_3$) consistent with structure.

C. The sulfonamide prepared in Example 18B (0.010 g, 0.019 mmol) was treated as described in Example 14E to give the crude amine-HCl salt. This material was subjected to the procedure described in Example 1D to give 6 mg (58% for two steps) of compound 234 after chromatography (CHCl$_3$/MeOH; 10:1). ([$^1$H]-NMR(CDCl$_3$) consistent with structure.

EXAMPLE 19

Synthesis of Compound 235

A. 4-Methoxybenzenesulfonyl chloride (0.035 g, 0.169 mmol) was dissolved in pyridine and 4-amino-1,2,4-triazole (0.17 g, 0.202 mmol) was added. After 4 days at R.T. the mixture was subjected to standard work-up conditions to give 33 mg of sulfonamide.

B. The sulfonamide prepared in Example 19A (0.356 g, 0.140 mmol) was treated with KOH (0.078 g, 0.139 mmol) to give the corresponding potassium salt.

C. The epoxide VI (W=Boc, Q=H) (0.049 g, 0.168 mmol) and the potassium salt of the amine prepared in Example 19B (0.044 g, 0.169 mmol) were reacted in DMSO at 80 ° C. for 2 days to give 9 mg (10%) of Boc-amine. [$^1$H]-NMR (CDCl$_3$) consistent with structure.

D. The sulfonamide prepared in Example 19C (0.143 g, 0.276 mmol) was treated as described in Example 14E to give the crude amine-HCl salt. This material was subjected to the procedure described in Example 1D to give 97 mg (66% for two steps) of compound 235 after recrystallization (CH$_2$Cl$_2$/MeOH). ([$^1$H]-NMR(CDCl$_3$) consistent with structure.

EXAMPLE 20

Synthesis of Compounds 167 and 168

A. Compound 167. A solution of 102 mg of N-((2 syn, 3S)-2-hydroxy-4-phenyl-3-((S)-tetrahydrofuran-3-yloxycarbonylamino)-butyl)-N-isobutylbenzenesulfonamide in 4:1 $CH_2Cl_2$/saturated aqueous $NaHCO_3$ was treated sequentially, at ambient temperature under an atmosphere of nitrogen, with 65 mg of p-nitrobenzenesulfonyl chloride and 51 mg of sodium bicarbonate. The mixture was stirred for 14 h, diluted with $CH_2Cl_2$, washed with saturated NaCl, then dried over $MgSO_4$, filtered, and concentrated in vacuo. The residue was purified by low pressure silica gel chromatography using 20% diethyl ether/$CH_2Cl_2$ as eluent to provide 124 mg of the title product as a white solid. TLC: Rf=0.36, 20% diethyl ether/$CH_2Cl_2$. HPLC: Rt=15.15 min. ($^1$H)-NMR ($CDCl_3$) consistent with structure.

B. Compound 168. A solution of 124 mg of compound 167 in ethyl acetate was treated, at ambient temperature, with 13 mg of 10% palladium on carbon. The mixture was stirred for 14 h under an atmosphere of hydrogen, filtered through a pad of Celite filter agent, and concentrated in vacuo. The residue was subjected to preparative HPLC to yield 82 mg of the title product as a white solid. TLC: Rf=0.10, 20% ether/$CH_2Cl_2$. HPLC: Rt=13.16 min. ($^1$H)-NMR ($CDCl_3$) consistent with structure.

EXAMPLE 21

We measured the inhibition constants of the compounds listed in Table II against HIV-1 protease using the above-cited method of Pennington et al.

We also measured the anti-viral potency of the compounds in CCRM-CEM cells by the above-cited method of Meek et al. The results are shown in Table III. In the Tables below, $K_i$ and $IC_{90}$ values are expressed in nM. The designation "ND" is used where a given compound was not tested.

In Table III, the following classifications have been employed:

A: inhibits HIV replication at concentration of 100 nM or less.

B: inhibits HIV replication at concentration of between 101 and 1,000 nM.

C: inhibits HIV replication at a concentration of between 1,001 and 10,000 nM.

D: inhibits HIV replication at a concentration of between 10,001 and 40,000 nM.

TABLE II

| Compound | $K_i$ | Compound | $K_i$ | Compound | $K_i$ |
|---|---|---|---|---|---|
| 35 | 4.0 | 168 | 0.6 | 229 | 11.0 |
| 37 | 0.1 | 169 | <0.1 | 230 | 9,300 |
| 48 | 1.4 | 170 | 0.2 | 231 | 1,400 |
| 51 | ND | 171 | 0.2 | 232 | 20.0 |
| 52 | 0.4 | 172 | 21 | 233 | 4.0 |
| 53 | 27 | 173 | 0.6 | 234 | 10,000 |
| 54 | 22 | 174 | 10 | 235 | 1,700 |
| 60 | 4.0 | 175 | 0.1 | 236 | 700.0 |
| 66 | 0.4 | 176 | <0.1 | 237 | ND |
| 69 | 42 | 180 | <0.1 | | |
| 86 | 5.0 | 181 | 0.3 | | |
| 88 | 1.4 | 182 | 0.2 | | |
| 91 | 2.5 | 183 | 0.1 | | |

TABLE II-continued

| Compound | $K_i$ | Compound | $K_i$ | Compound | $K_i$ |
|---|---|---|---|---|---|
| 93 | 0.8 | 195 | 0.2 | | |
| 94 | 1.7 | 196 | ND | | |
| 95 | 1.3 | 197 | <.1 | | |
| 99 | 0.24 | 198 | <.1 | | |
| 100 | 0.16 | 199 | 10.0 | | |
| 101 | 250 | 200 | 2.4 | | |
| 112 | 4.0 | 201 | 7.5 | | |
| 113 | 3.0 | 202 | .1 | | |
| 116 | <0.1 | 203 | 60.0 | | |
| 123 | 10 | 204 | 4.0 | | |
| 124 | 1.1 | 205 | 5.0 | | |
| 125 | 0.3 | 206 | .50 | | |
| 132 | 6.0 | 207 | 33.0 | | |
| 133 | 24 | 208 | 5.5 | | |
| 134 | 8.4 | 209 | .8 | | |
| 135 | 2.7 | 210 | 6.0 | | |
| 136 | 18 | 211 | <0.1 | | |
| 137 | 26 | 212 | 1.0 | | |
| 138 | 1.4 | 213 | 5.0 | | |
| 140 | <0.1 | 214 | 110.0 | | |
| 144 | 8.0 | 215 | 11.0 | | |
| 145 | 1.4 | 216 | <0.1 | | |
| 148 | 0.2 | 217 | 0.3 | | |
| 149 | 1.7 | 218 | 5.0 | | |
| 150 | 6.0 | 219 | 1.0 | | |
| 151 | 0.8 | 220 | 0.2 | | |
| 152 | 2.5 | 221 | 1.0 | | |
| 157 | 0.7 | 222 | 0.5 | | |
| 158 | <0.1 | 223 | 3,800 | | |
| 159 | 0.2 | 224 | 1.0 | | |
| 160 | 1.0 | 225 | 1,500 | | |
| 161 | 20 | 226 | 3,000 | | |
| 165 | 0.4 | 227 | 9.0 | | |
| 167 | 0.45 | 228 | 4,550 | | |

TABLE III

| Compound | $IC_{90}$ | Compound | $IC_{90}$ |
|---|---|---|---|
| 35 | B | 169 | A |
| 37 | B | 170 | B |
| 48 | B | 171 | A |
| 51 | C | 172 | ND |
| 52 | B | 173 | A |
| 53 | ND | 174 | ND |
| 60 | C | 175 | A |
| 66 | B | 176 | ND |
| 69 | ND | 180 | ND |
| 86 | B | 181 | ND |
| 88 | B | 182 | B |
| 91 | B | 183 | B |
| 93 | B | 195 | A |
| 94 | B | 196 | ND |
| 95 | C | 197 | ND |
| 99 | B | 198 | ND |
| 100 | A | 199 | ND |
| 101 | ND | 200 | ND |
| 112 | B | 201 | ND |
| 113 | B | 202 | ND |
| 116 | A | 203 | ND |
| 123 | ND | 204 | ND |
| 124 | D | 205 | ND |
| 125 | B | 206 | B |
| 132 | ND | 207 | ND |
| 133 | ND | 208 | ND |
| 134 | ND | 209 | B |
| 135 | C | 210 | ND |
| 136 | ND | 211 | A |
| 137 | ND | 212 | B |
| 138 | B | 213 | ND |
| 140 | A | 214 | ND |
| 144 | B | 215 | ND |
| 145 | B | 216 | A |

TABLE III-continued

| Compound | IC₉₀ | Compound | IC₉₀ |
|---|---|---|---|
| 148 | A | 217 | A |
| 149 | B | 218 | ND |
| 150 | B | 219 | A |
| 151 | C | 220 | A |
| 152 | ND | 221 | B |
| 157 | B | 222 | ND |
| 158 | A | 223 | ND |
| 159 | B | 224 | ND |
| 160 | A | 225 | ND |
| 161 | ND | 226 | ND |
| 165 | B | 227 | ND |
| 167 | B | 228 | ND |
| 168 | A | 229 | ND |
| 230 | ND | | |
| 231 | ND | | |
| 232 | ND | | |
| 233 | ND | | |
| 234 | ND | | |
| 235 | ND | | |
| 236 | ND | | |
| 237 | ND | | |

As demonstrated in Tables II and III, all of the compounds tested displayed inhibitory and anti-viral activity. Moreover, several of these compounds exhibited activity levels which are among the highest levels known to date for HIV protease inhibitors.

While we have described a number of embodiments of this invention, it is apparent that our basic constructions may be altered to provide other embodiments which utilize the products and methods of this invention. Therefore, it will be appreciated that the scope of this invention is to be defined by the appended claims, rather than by the specific embodiments which have been presented by way of example.

We claim:

1. A pharmaceutical composition comprising:
   a) a pharmaceutically effective amount of a compound of the formula:

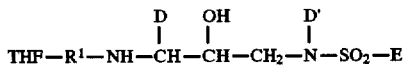

$$\text{THF}-R^1-NH-\overset{\overset{D}{|}}{CH}-\overset{\overset{OH}{|}}{CH}-CH_2-\overset{\overset{D'}{|}}{N}-SO_2-E \quad (I)$$

wherein;

each $R^1$ is independently selected from the group consisting of —C(O)—, —S(O)$_2$—, —C(O)—C(O)—, —O—C(O)—, —O—S(O)$_2$, —NR$^2$—S(O)$_2$—, —NR$^2$—C(O)— and —NR$^2$—C(O)—C(O)—;

each Het is independently selected from the group consisting of $C_3$–$C_7$ carbocycle; $C_6$–$C_{10}$ aryl; phenyl fused with heterocycle; and heterocycle; wherein any member of said Het may be optionally substituted with one or more substituents selected from the group consisting of oxo, —OR$^2$, —R$^2$, —N(R$^2$)(R$^2$), —NHOH, —R$^2$—OH, —CN, —CO$_2$R$^2$, —C(O)—N(R$^2$)(R$^2$), —S(O)$_2$—N(R$^2$)(R$^2$), —N(R$^2$)—C(O)—R$^2$, —C(O)—R$^2$, —S(O)$_n$—R$^2$, —OCF$_3$, —S(O)$_n$—R$^6$, —N(R$^2$) —S(O)$_2$(R$^2$), halo, —CF$_3$, —NO$_2$, —R$^6$ and —O—R$^6$;

each $R^2$ is independently selected from the group consisting of H and $C_1$–$C_3$ alkyl optionally substituted with $R^6$;

each $R^3$ is independently selected from the group consisting of H, Het, $C_1$–$C_6$ alkyl and $C_2$–$C_6$ alkenyl wherein any member of said $R^3$, except H, may be optionally substituted with one or more substituents selected from the group consisting of —OR$^2$, —C(O) —NH—R$^2$, —S(O)$_n$—N(R$^2$)(R$^2$), Het, —CN, —SR$^2$, —CO$_2$R$^2$, NR$^2$—C(O)—R$^2$;

each n is independently 1 or 2;

each D and D' is independently selected from the group consisting of R$^6$; $C_1$–$C_5$ alkyl, which may be optionally substituted with one or more groups selected from —OR$^2$, —R$^3$, —O—R$^6$, —S—R$^6$ and R$^6$; $C_2$–$C_4$ alkenyl, which may be optionally substituted with one or more groups selected from the group consisting of —OR$^2$, —R$^3$, —O—R$^6$ and R$^6$; $C_3$–$C_6$ carbocycle, which may be optionally substituted with or fused with R$^6$; and $C_5$–$C_6$ cycloalkenyl, which may be optionally substituted with or fused with R$^6$;

each E is independently selected from the group consisting of Het; —O—Het; Het—Het; —O—R$^3$; —NR$^2$R$^3$; $C_1$–$C_6$ alkyl, which may be optionally substituted with one or more groups selected from the group consisting of $R^4$ and Het; and $C_2$–$C_6$ alkenyl, which may be optionally substituted with one or more groups selected from the group consisting of $R^4$ and Het;

each $R^4$ is independently selected from the group consisting of —OR$^2$, —C(O)—NHR$^2$, —S(O)$_2$—NHR$^2$, halo, —NR$^2$—C(O)—R$^2$ and —CN;

each $R^5$ is independently selected from the group consisting of H and $C_1$–$C_4$ alkyl optionally substituted with aryl; and each $R^6$ is independently selected from the group consisting of aryl, carbocycle and heterocycle, wherein said carbocycle or heterocycle may be optionally substituted with one or more groups selected from the group consisting of oxo, —OR$^5$, —R$^5$, —N(R$^5$) (R$^5$), —N(R$^5$)—C(O)—R$^5$, —R$^5$—OH, —CN, —CO$_2$R$^5$, —C(O)—N(R$^5$) (R$^5$), halo and —CF$_3$;

b) one or more additional agents selected from the group consisting of other anti-viral agents and immunostimulators; and c) a pharmaceutically acceptable carrier, adjuvant or vehicle, wherein said pharmaceutical composition is orally administrable.

2. The pharmaceutical composition according to claim 1, wherein said other anti-viral agent or agents are protease inhibitors or reverse transcriptase inhibitors.

3. The pharmaceutical composition according to claim 2, wherein said protease inhibitor or inhibitors are HIV protease inhibitors.

4. The pharmaceutical composition according to claim 3, wherein said HIV protease inhibitor or inhibitors are selected from the group consisting of saquinavir (Ro 31-8959), MK 639, ABT 538 (A80538), AG 1343, XM 412, XM 450 and BMS 186,318.

5. The pharmaceutical composition according to claim 2, wherein said reverse transcriptase inhibitor or inhibitors are nucleoside analogs.

6. The pharmaceutical composition according to claim 5, wherein said nucleoside analog or analogs are selected from the group consisting of zidovudine (AZT), dideoxycytidine (ddC), didanosine (ddI), stavudine (d4T), 3TC, 935U83, 1592U89 and 524W91.

7. The pharmaceutical composition according to claim 2, wherein said reverse transcriptase inhibitor or inhibitors are non-nucleoside analogs.

8. The pharmaceutical composition according to claim 7, wherein said non-nucleoside reverse transcriptase inhibitor or inhibitors are delavirdine (U90) or nevirapine.

9. A method for preventing HIV infection in a mammal comprising the step of administering to said mammal a pharmaceutically effective amount of a pharmaceutical composition according to claim 1.

10. A method for treating HIV infection in a mammal comprising the step of administering to said mammal a pharmaceutically effective amount of a pharmaceutical composition according to claim 1.

11. A method of treating or preventing HIV infection in a mammal comprising the steps of:
a) administering to the mammal a composition comprising:
(i) a pharmaceutically effective amount of a compound of the formula:

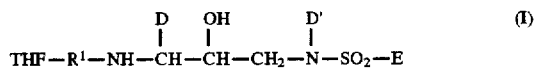

wherein:
each $R^1$ is independently selected from the group consisting of —C(O)—, —S(O)$_2$—, —C(O)—C(O)—, —O—C(O)—, —O—S(O)$_2$, —NR$^2$—S(O)$_2$—, —NR$^2$—C(O)— and —NR$^2$—C(O)—C(O)—;

each Het is independently selected from the group consisting of $C_3$—$C_7$ carbocycle; $C_6$–$C_{10}$ aryl; phenyl fused with heterocycle; and heterocycle; wherein any member of said Het may be optionally substituted with one or more substituents selected from the group consisting of oxo, —OR$^2$, —R$^2$, N(R$^2$) (R$^2$), —NHOH, —R$^2$—OH, —CN, —CO$_2$R$^2$, —C(O)—N(R)(R$^2$), —S(O)$_2$—N(R$^2$)(R$^2$), —N(R$^2$)—C(O)—R$^2$, —C(O)—R$^2$, —S(O)$_n$—R$^2$, —OCF$_3$, —S(O)$_n$—R$^6$, —N(R$^2$)—S(O)$_2$(R$^2$), halo, —CF$_3$, —NO$_2$, —R$^6$ and —O—R$^6$;

each $R^2$ is independently selected from the group consisting of H and $C_1$–$C_3$ alkyl optionally substituted with $R^6$;

each $R^3$ is independently selected from the group consisting of H, Het, $C_1$–$C_6$ alkyl and $C_2$–$C_6$ alkenyl wherein any member of said $R^3$, except H, may be optionally substituted with one or more substituents selected from the group consisting of —OR$^2$, —C(O)—NH—R$^2$, —S(O)$_n$—N(R$^2$)(R$^2$), Het, —CN, —SR$^2$, —CO$_2$R$^2$, NR$^2$—C(O)—R$^2$;

each n is independently 1 or 2;

each D and D' is independently selected from the group consisting of $R^6$; $C_1$–$C_5$ alkyl, which may be optionally substituted with one or more groups selected from —OR$^2$, —R$^3$, —O—R$^6$, —S—R$^6$ and R$^6$; $C_2$–$C_4$ alkenyl, which may be optionally substituted with one or more groups selected from the group consisting of —OR$^2$, —R$^3$, —O—R$^6$ and R$^6$; $C_3$–$C_6$ carbocycle, which may be optionally substituted with or fused with R$^6$; and $C_5$–$C_6$ cycloalkenyl, which may be optionally substituted with or fused with R$^6$;

each E is independently selected from the group consisting of Het; —O—Het; Het—Het; —O—R$^3$; —NR$^2$R$^3$; $C_1$–$C_6$ alkyl, which may be optionally substituted with one or more groups selected from the group consisting of R$^4$ and Het; and $C_2$–$C_6$ alkenyl, which may be optionally substituted with one or more groups selected from the group consisting of R$^4$ and Het;

each $R^4$ is independently selected from the group consisting of —OR$^2$, —C(O)—NHR$^2$, —S(O)$_2$—NHR$^2$, halo, —NR$^2$—C(O)—R$^2$ and —CN;

each $R^5$ is independently selected from the group consisting of H and $C_1$–$C_4$ alkyl optionally substituted with aryl; and each $R^6$ is independently selected from the group consisting of aryl, carbocycle and heterocycle, wherein said carbocycle or heterocycle may be optionally substituted with one or more groups selected from the group consisting of oxo, —OR$^5$, —R$^5$, —N(R$^5$)(R$^5$), —N(R$^5$)—C(O)—R$^5$, —R$^5$—OH, —CN, —CO$_2$R$^5$, —C(O)—N(R$^5$)(R$^5$), halo and —CF$_3$; and ii) a pharmaceutically acceptable carrier, adjuvant or vehicle, wherein said pharmaceutical composition is orally administrable; and b) concurrently or sequentially administering to the mammal one or more additional agents selected from the group consisting of other anti-viral agents and immunostimulators.

12. The method according to claim 11, wherein said other anti-viral agent or agents are protease inhibitors or reverse transcriptase inhibitors.

13. The method according to claim 12, wherein said protease inhibitor or inhibitors are protease inhibitors.

14. The method according to claim 13, wherein said HIV protease inhibitor or inhibitors are selected from the group consisting of saquinavir (Ro 31-8959), MK 639, ABT 538 (A80538), AG 1343, XM 412, XM 450 and BMS 186,318.

15. The method according to claim 11, wherein said reverse transcriptase inhibitor or inhibitors are nucleoside analogs.

16. The method according to claim 15, wherein said nucleoside analog or analogs are selected from the group consisting of zidovudine (AZT), dideoxycytidine (ddC), didanosine (ddI), stavudine (d4T), 3TC, 935U83, 1592U89 and 524W91.

17. The method according to claim 12, wherein said reverse transcriptase inhibitor or inhibitors are non-nucleoside analogs.

18. The method according to claim 17, wherein said non-nucleoside reverse transcriptase inhibitor or inhibitors are delavirdine (U90) or nevirapine.

* * * * *

UNITED STATES PATENT AND TRADEMARK OFFICE
CERTIFICATE OF CORRECTION

PATENT NO. : 5,723,490
DATED : March 3, 1998
INVENTOR(S) : Roger D. Tung

It is certified that error appears in the above-identified patent and that said Letters Patent is hereby corrected as shown below:

On title page, item [63], under Related U.S. Application Data, delete "Nov. 24, 1993," and substitute therefor -- Sept. 7, 1993, --.

On title page, item [56], under OTHER PUBLICATIONS, in "M. Cushman", delete "Delvelopment" and substitute therefor -- Development --.

On title page, item [56], under OTHER PUBLICATIONS, in "G.B. Dreyer", delete "Isosters" and substitute therefor -- Isostere --.

On page 2, item [56], under OTHER PUBLICATIONS, in "X. Lin", delete "Enzymatic" and substitute therefor -- "Enzymic --.

Column 1, line 10, delete "Nov. 24, 1993;" and substitute therefor -- Sept. 7, 1993; --.

Column 3, line 1, delete "-N($R^2$) S(O)$_2$($R^2$)," and substitute therefor -- -N($R^2$)-S(O)$_2$($R^2$), --.

Column 4, line 13, delete "tertrahydropyran" and substitute therefor -- tetrahydropyran --.

Column 6, line 53, immediately after "silyl" insert -- groups --.

Column 9, line 7, delete "-(O)-C(O)-," and substitute therefor -- -C(O)-C(O)-, --.

UNITED STATES PATENT AND TRADEMARK OFFICE
CERTIFICATE OF CORRECTION

PATENT NO.  : 5,723,490
DATED       : March 3, 1998
INVENTOR(S) : Roger D. Tung

It is certified that error appears in the above-identified patent and that said Letters Patent is hereby corrected as shown below:

Column 9, line 8, delete "-$NR_2$-C(O)-" and substitute therefor -- -$NR^2$-C(O)- --.

Column 9, line 9, delete "-$NR_2$-C(O)-C(O)-;" and substitute therefor -- -$NR^2$-C(O)-C(O)-; --.

Column 10, line 18, delete "-S(O)$NHR^2$,-" and substitute therefor -- -S(O)$_2NHR^2$, --.

Columns 25-26, under D' compound #224, delete "  " and substitute therefor --  --.

Column 33, line 8, delete "functionalites" and substitute therefor -- functionalities --.

Column 34, line 54, immediately after "other" insert -- HIV--.

Column 39, line 10, delete "compounds" and substitute therefor -- compounds' --.

Column 40, line 59, delete "$CDCl_2$)," and substitute therefor -- $CH_2Cl_2$), --.

UNITED STATES PATENT AND TRADEMARK OFFICE
CERTIFICATE OF CORRECTION

PATENT NO. : 5,723,490
DATED : March 3, 1998
INVENTOR(S) : Roger D. Tung

It is certified that error appears in the above-identified patent and that said Letters Patent is hereby corrected as shown below:

Column 41, line 6, delete "yeld" and substitute therefor -- yield --.

Column 41, line 8, delete "$m_9$" and substitute therefor -- mg --.

Column 41, line 32, immediately after "followed" insert -- by --.

Column 41, line 44, delete "(W=E," and substitute therefor -- (W=H, --.

Column 42, line 51, immediately after "solution" insert -- of --.

Column 44, line 49, delete the first occurrence of "the" and substitute therefor -- then --.

Column 46, line 62, delete "Chormotography" and substitute therefor -- Chromatography --.

Column 54, line 60, delete "non-nucleo side" and substitute therefor -- non-nucleoside --.

Column 55, line 26, delete "C(O)-N(R)$(R^2)$," and substitute therefor -- -C(O)-N($(R^2)$)$(R^2)$, --.

Column 56, line 33, immediately after "or inhibitors are" insert -- HIV --.

Column 56, line 38, delete "11," and substitute therefor -- 12, --.

UNITED STATES PATENT AND TRADEMARK OFFICE
CERTIFICATE OF CORRECTION

PATENT NO. : 5,723,490
DATED : March 3, 1998
INVENTOR(S) : Roger D. Tung

It is certified that error appears in the above-identified patent and that said Letters Patent is hereby corrected as shown below:

Column 53, line 38, delete ";" and substitute therefor -- : --.

Column 53, line 43, delete ";" and substitute therefor -- : --.

Signed and Sealed this

Twenty-second Day of May, 2001

Attest:

NICHOLAS P. GODICI

Attesting Officer

Acting Director of the United States Patent and Trademark Office